(12) United States Patent
Lalonde et al.

(10) Patent No.: US 12,208,390 B2
(45) Date of Patent: *Jan. 28, 2025

(54) METHODS, DEVICES, AND SYSTEMS FOR DETECTING ANALYTES

(71) Applicant: GRIP Molecular Technologies, Inc., St. Paul, MN (US)

(72) Inventors: John Lalonde, Irvine, CA (US); Bruce Edgar Batten, Shoreview, MN (US)

(73) Assignee: GRIP Molecular Technologies, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/127,933

(22) Filed: Mar. 29, 2023

(65) Prior Publication Data
US 2023/0294092 A1  Sep. 21, 2023

Related U.S. Application Data

(63) Continuation of application No. 16/147,300, filed on Sep. 28, 2018, now Pat. No. 11,666,907.

(60) Provisional application No. 62/572,302, filed on Oct. 13, 2017, provisional application No. 62/566,141, filed on Sep. 29, 2017.

(51) Int. Cl.
| | |
|---|---|
| *B01L 3/00* | (2006.01) |
| *C12Q 1/6825* | (2018.01) |
| *G01N 21/63* | (2006.01) |
| *G01N 21/77* | (2006.01) |
| *G01N 27/12* | (2006.01) |
| *G01N 33/487* | (2006.01) |
| *G01N 27/414* | (2006.01) |

(52) U.S. Cl.
CPC ...... *B01L 3/502715* (2013.01); *C12Q 1/6825* (2013.01); *G01N 21/63* (2013.01); *G01N 21/77* (2013.01); *G01N 27/122* (2013.01); *G01N 27/125* (2013.01); *G01N 33/48721* (2013.01); *B01L 2200/10* (2013.01); *B01L 2300/023* (2013.01); *B01L 2300/0663* (2013.01); *G01N 27/128* (2013.01); *G01N 27/4145* (2013.01)

(58) Field of Classification Search
None
See application file for complete search history.

(56) References Cited

U.S. PATENT DOCUMENTS

| | | | |
|---|---|---|---|
| 9,096,823 B1 | 8/2015 | Branch et al. | |
| 11,666,907 B2 * | 6/2023 | Lalonde | G01N 21/77 436/501 |
| 2013/0248380 A1 | 9/2013 | Cui | |
| 2014/0174927 A1 | 6/2014 | Bashir et al. | |
| 2017/0018626 A1 * | 1/2017 | Hoffman | G01N 27/4146 |

FOREIGN PATENT DOCUMENTS

| | | | |
|---|---|---|---|
| CN | 106442679 | * | 2/2017 |
| WO | WO2011004136 A1 | | 1/2011 |

* cited by examiner

*Primary Examiner* — Ann Montgomery
(74) *Attorney, Agent, or Firm* — Bret E. Field; Bozicevic, Field & Francis LLP

(57) ABSTRACT

This document provides methods, devices, and systems for detecting the presence, absence, or amount of one or more analytes. For example, this document provides methods for using graphene-based sensors to detect one or more analytes (e.g., proteins, nucleic acids, intact cells, intact viruses, intact microorganisms, and/or chemicals).

19 Claims, 17 Drawing Sheets

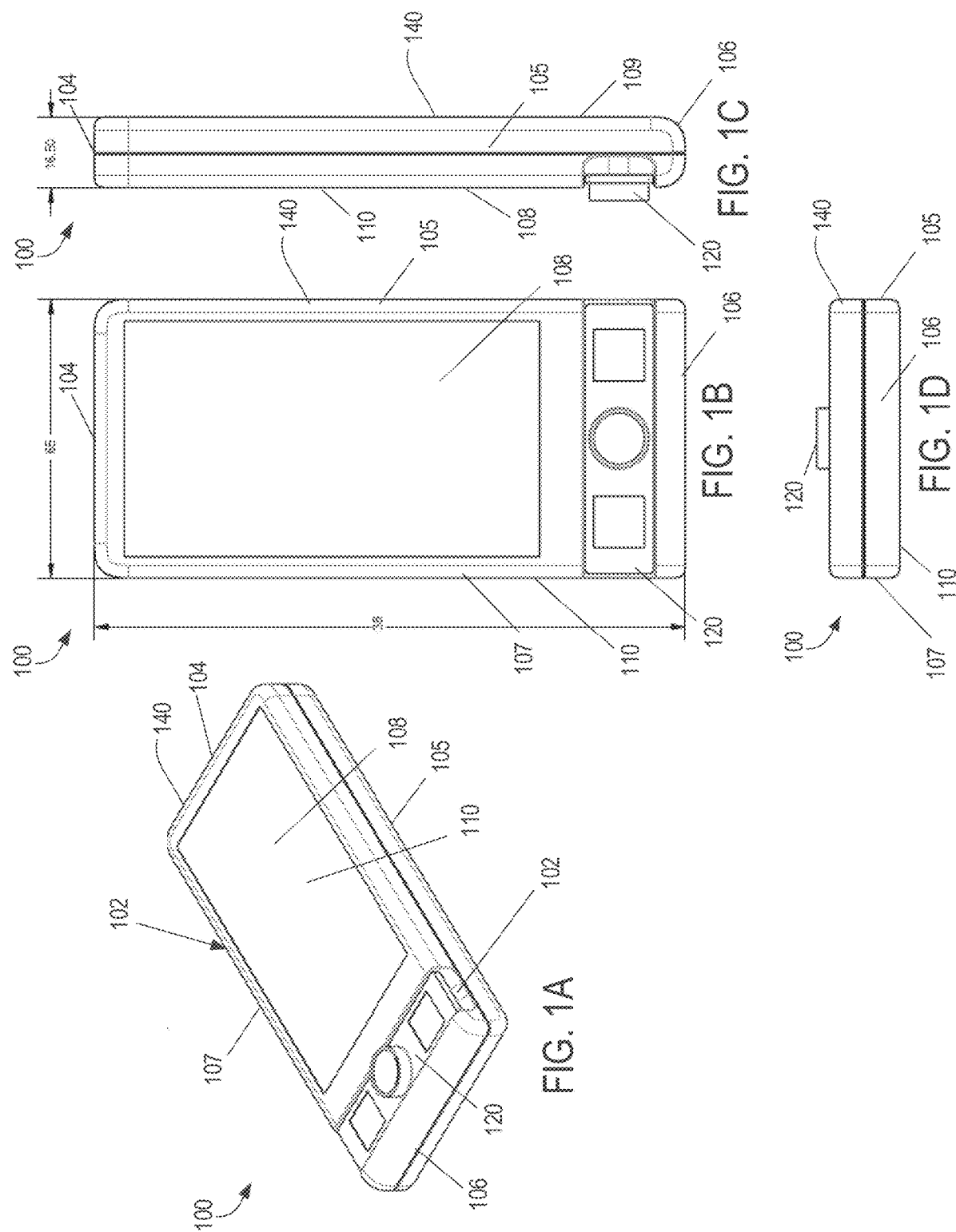

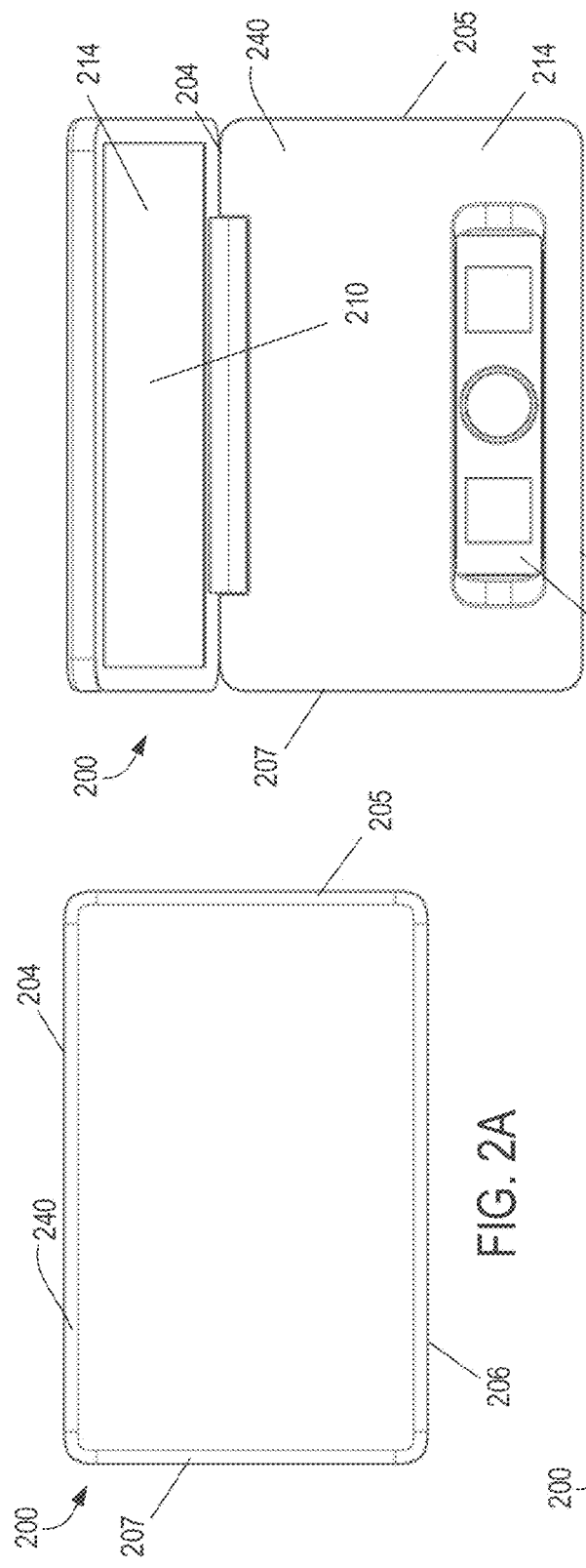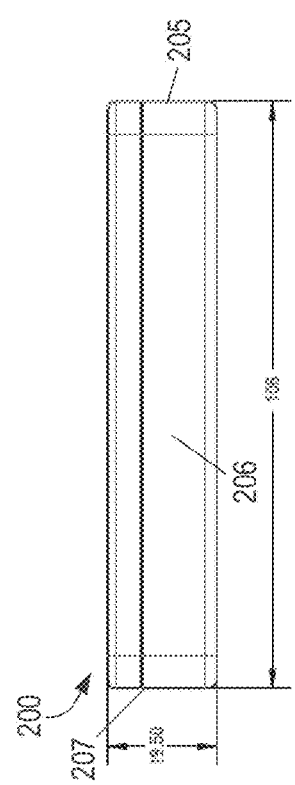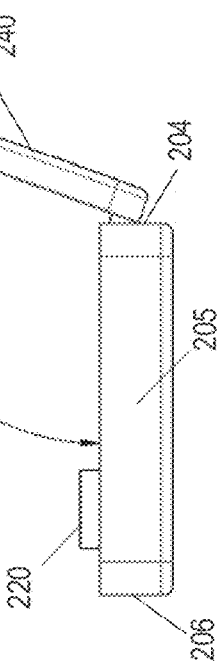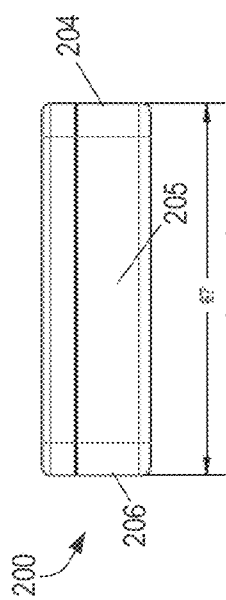

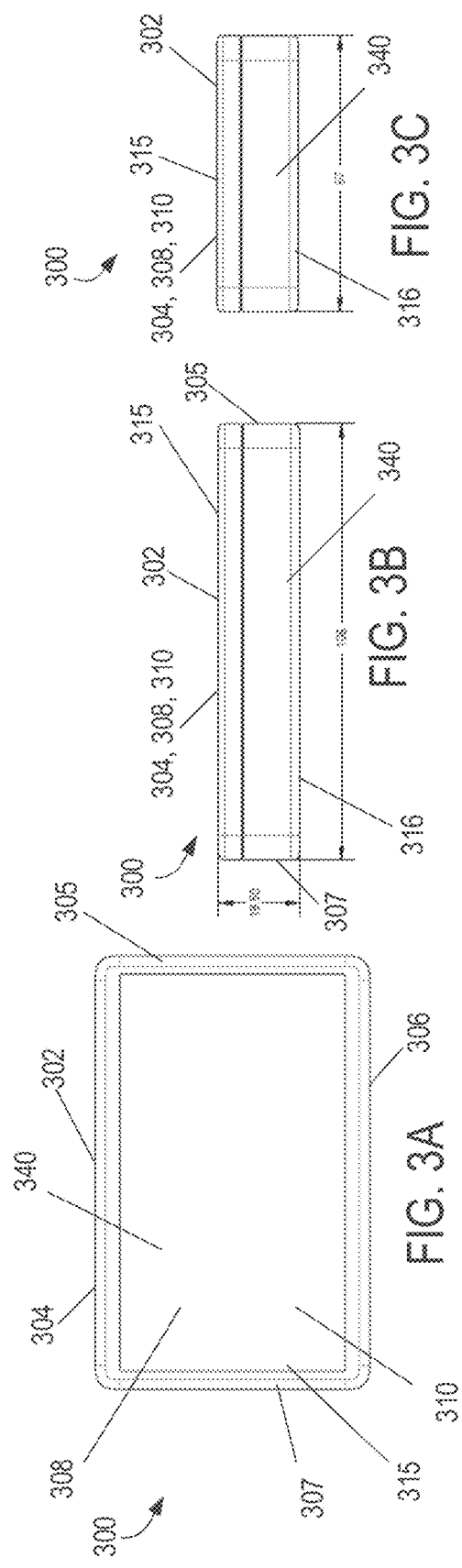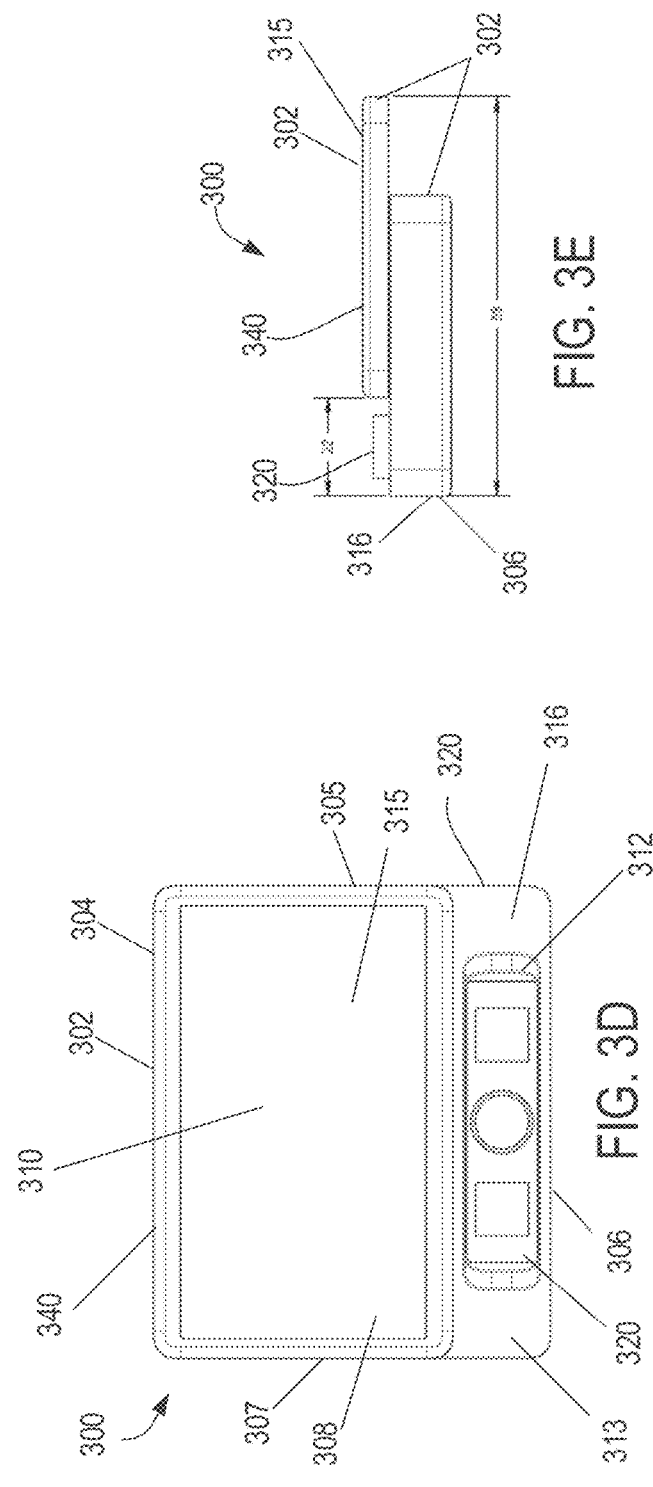

METHODS, DEVICES, AND SYSTEMS FOR DETECTING ANALYTES

CROSS REFERENCE TO RELATED APPLICATION

This application is a continuation of U.S. patent application Ser. No. 16/147,300 filed Sep. 28, 2018, now issued as U.S. Pat. No. 11,666,907, which application claims the benefit of U.S. Provisional Patent Application No. 62/566,141 filed Sep. 29, 2017 and U.S. Provisional Patent Application No. 62/572,302 filed Oct. 13, 2017; the disclosures of which applications are herein incorporated by reference in its entirety.

BACKGROUND

Technical Field

This document relates to methods, devices, and systems for detecting the presence, absence, or amount of one or more analytes. For example, this document provides methods for using graphene-based sensors to detect one or more analytes (e.g., proteins, nucleic acids, intact cells, intact viruses, intact microorganisms, and/or chemicals) as well as devices (e.g., graphene-based analyte sensor devices) and systems designed to detect one or more analytes (e.g., proteins, nucleic acids, intact cells, intact viruses, intact microorganisms, and/or chemicals).

Background Information

Field-effect transistor (FET) biosensors respond to a biological environment to produce a readable signal. FET-based biosensors have been used to detect biomolecules, for example, DNA and bacterium, and biological conditions, such as pH conditions. Biomolecule detection in a sample provides valuable information for various medical applications, including biomedical diagnostics, drug screening, environmental contamination, and food safety evaluation, and drug discovery applications.

SUMMARY

This document provides methods, devices, and systems for detecting the presence, absence, or amount of one or more analytes. For example, this document provides methods for using graphene-based sensors to detect one or more analytes (e.g., proteins, nucleic acids, intact cells, intact viruses, intact microorganisms, and/or chemicals). As described herein, a sample can be obtained and inserted into a processing/sensing unit (PSU). In some cases, a PSU provided herein can be designed to be a self-contained unit capable of receiving a sample (e.g., a biological sample), docking into a master control unit (MCU), performing processing steps designed to prepare the sample or components within the sample for detection, generating raw electronic signals related to the presence, absence, or amount of one or more analytes in the sample (e.g., processed sample) via a sensor (e.g., a graphene-based sensor), converting the raw electronic signals into raw digital data, sending the raw digital data related to the presence, absence, or amount of one or more analytes in the sample to the MCU, and/or retaining the received sample for safe and clean disposal. In some cases, a PSU provided here can be designed to have a height from about 2 mm to about 8 mm, a length from about 30 mm to about 80 mm, and a depth from about 15 mm to about 50 mm. The PSU may only perform these activities when coupled with the MCU in some scenarios, while in other scenarios the PSU may be "powered" and be able produce digital data and send it the MCU.

Once a sample is inserted into a PSU provided herein, the PSU can be attached to or docked into an MCU. In some cases, an MCU provided herein can be a portable, hand-held unit capable of receiving a PSU containing a sample to be analyzed, providing power to the received PSU, receiving digital data (e.g., raw digital data) from the PSU, processing the received digital data received from the PSU to determine the presence, absence, or amount of one or more analytes in the sample, communicating information about the presence, absence, or amount of one or more analytes in the sample to a user or other person directly from the MCU, and/or transmitting information about the presence, absence, or amount of one or more analytes in the sample over a network (e.g., local area network (LAN), wide area network (WAN), internet, wireless network, wired network, virtual private network (VPN), mobile data network (e.g., 4G network), and/or combinations thereof) to a server system (e.g., cloud-based server system) and/or another electronic device (e.g., smartphone, laptop computer, or desktop computer). In some cases, an MCU provided here can be designed to have a height from about 1.5 cm to about 2.5 cm, a length from about 12 cm to about 15 cm, and a depth from about 5 cm to about 8 cm.

After the PSU is attached to an MCU, the sample can be processed within the PSU to prepare the sample or components within the sample for detection. For example, a sample containing cells can be subjected to one or more cell lysis procedures within the PSU itself to prepare cellular components such as nucleic acid for detection.

Once the sample is processed in a manner to prepare the sample (or components within the sample) for detection, the sample (or components within the sample) can be placed in contact with a sensor (e.g., a graphene-based sensor) to detect the presence, absence, or amount of one or more analytes in the sample. For example, a sample containing cells can be lysed, and the resulting cell lysis material, which can include cellular nucleic acid, can be contacted with a graphene-based sensor having one or more immobilized (examples of attachment include but are not limited to ionic bonding, pi-pi binding, sigma binding, covalent bonding, polar bonding, electrostatic bonding) capture agents designed to bind to one or more particular nucleic acid analytes that might be present within the sample. Electrical current applied to a graphene-based sensor having one or more immobilized capture agents can generate raw electronic signals based on the binding (or lack thereof) of an analyte of interest to an immobilized capture agent. For example, nucleic acid hybridization of a nucleic acid of interest present within a sample being analyzed to a complementary nucleic acid capture agent attached to a graphene-based sensor present within the PSU can generate raw electronic signals indicative of such hybridization, while the lack of such hybridization can generate raw electronic signals indicative of a lack of such hybridization. In some cases, the raw electronic signals generated within the PSU can be converted into raw digital data within the PSU. For example, a PSU provided herein can include an application-specific integrated circuit (ASIC) designed to detect the generated raw electronic signals and convert them into raw digital data. In some cases, the raw digital data can be sent to the MCU or another device (e.g., cloud-based server system, laptop, desktop computer, mobile computing device, such as a smartphone, wearable computing device, and/or tablet computing device). For example, raw digital data related to the raw electronic signals generated by a graphene-based sensor can be sent or transmitted to the MCU without being analyzed to determine if the raw digital data are indicative of the presence, absence, or amount of the analyte being assessed.

After an MCU receives raw digital data from a PSU provided herein, the MCU can process the received raw digital data to determine if the raw digital data is indicative of the presence or absence of one or more analytes in the sample. For example, the MCU can assess the nature (e.g., the frequency, strength, time sequence, and/or signature) of particular received raw digital data over time to determine that an analyte was present within the sample. In some cases, the MCU can process the received raw digital data in a manner that determines that an analyte of interest is not present within the sample based on minimal changes, or a lack of any changes, in the raw digital data over the time of the sample analysis. In some cases, the MCU can process the received raw digital data to determine the amount of one or more analytes in the sample. For example, the MCU can assess the nature (e.g., the frequency, strength, time sequence, and/or signature) of particular received raw digital data over time to determine that a particular amount of an analyte of interest is present within the sample.

After the MCU processes raw digital data received from a PSU provided herein to determine the presence, absence, or amount of one or more analytes in the sample, the MCU can communicate information about the presence, absence, or amount of one or more analytes in the sample to a user or other person directly from the MCU. For example, an MCU can include a display unit and can display information about the presence, absence, or amount of one or more analytes in the sample to a user or other person directly via the display unit. In some cases, an MCU can transmit information about the presence, absence, or amount of one or more analytes in the sample over a network (e.g., LAN, WAN, wireless network, wired network, internet. VPN, mobile data network, cellular network, BLUETOOTH network, and/or combinations thereof) to a server system (e.g., cloud-based server) and/or another electronic device (e.g., smartphone, laptop computer, or desktop computer). For example, an MCU can include a wireless communication transmitter (e.g., a radio transmitter such as a BLUETOOTH transmitter, a Wi-Fi transmitter, a near field communication (NFC) transmitter, a mobile data network (e.g., 4G network, LTE network) transmitter) and can transmit information about the presence, absence, or amount of one or more analytes in the sample over a network (e.g., LAN, WAN, wireless network, wired network, internet. VPN, mobile data network, cellular network. BLUETOOTH network, and/or combinations thereof) to a server system (e.g., cloud-based server) and/or another electronic device (e.g., a user's smartphone). In some cases, an MCU can be configured to (a) communicate information about the presence, absence, or amount of one or more analytes in the sample to a user or other person directly from the MCU only, (b) transmit information about the presence, absence, or amount of one or more analytes in the sample to a network, server, or another electronic device only, or (c) both communicate information about the presence, absence, or amount of one or more analytes in the sample to a user or other person directly from the MCU and transmit information about the presence, absence, or amount of one or more analytes in the sample to a network, server, or another electronic device.

In some cases, the sample inserted into the PSU, after being processed and analyzed, can be retained within the PSU for safe and clean disposal. For example, a PSU provided herein can be a disposable, self-contained unit that is capable of receiving a sample to be assessed and retaining the sample without leakage from the PSU and/or without contaminating other surfaces, components, or people (e.g., without contaminating an MCU used with the PSU).

In some cases, a PSU can be designed to have one or more assay channels (e.g., 1, 2, 3, 4, 5, 6, 7, 8, 9, 10, 11, 12, 16, 64, 128, 192, 256, 512, or more assay channels). For example, a PSU described herein can be designed to have from about 100 assay channels to about 500 assay channels. For example, a PSU described herein can be designed to have 16, 64, 128, 192, 256, or 512 assay channels. Each assay channel can include an input region configured to receive a portion of a sample inserted into the PSU, a processing region configured to prepare the sample or components within the sample for detection (e.g., a cell lysis region configured to lyse cells within a sample), and a detection region configured to include a sensor (e.g., a graphene-based sensor) having a capture agent capable of binding to an analyte of interest. In some cases, a PSU described herein can include an ASIC having a dedicated analog-to-digital signal processing unit for each detection region. For example, an ASIC can have multiple dedicated analog-to-digital signal processing units that correspond to the multiple assay channels, with each analog-to-digital signal processing unit including a signal amplifier, an analog-to-digital converter (ADC), a digital filter, a buffer, and I/O interface for flushing data stored in the buffer out through one or more busses on the ASIC. In some cases, such an ASIC can be designed to control one or more processing steps to be performed within a processing region of a PSU. For example, the ASIC can include a control unit that controls the analog-to-digital processing units and selectively flushes the buffers from each of the analog-to-digital processing units for processing by the PSU, the MSU, a remote computing device/system (e.g., mobile computing device, cloud-based server system), and/or combinations thereof. As described herein, each assay channel of a PSU described herein can be designed to detect a different analyte. For example, a PSU described herein can be designed to have one or more assay channels (e.g., 1, 2, 3, 4, 5, 6, 7, 8, 9, 10, 11, 12, 16, 64, 128, 192, 256, 512, or more assay channels), and each detection region of those one or more assay channels can include a sensor (e.g., a graphene-based sensor) having a different capture agent. In some cases, multiple assay channels (e.g., two, three, four, five, or more assay channels) of a single PSU can be designed to detect the same analyte (e.g., protein, nucleic acid, intact cell, intact virus, intact microorganism, or chemical) using either the same capture agent for that analyte or different capture agents for that analyte. For example, two or more different antibodies that have the ability to bind to the same protein can be used is separate assay channels to detect that protein. In such cases, the MCU can be designed to process the raw digital data for each of those assay channels either separately or as a group to make a determination about the presence, absence, or amount of that protein within the sample.

In some cases, the longest dimension of an assay channel of a PSU described herein can be less than 2 mm (e.g., or less than 5 mm, 10 mm, 15 mm, 20 mm, 30 mm, or 40 mm). In some cases, the distance between a processing region (e.g., a cell lysis region configured to lyse cells via, for example, sonication) of one assay channel and a detection region of that same assay channel can be from about 50 μm to about 300 mm. As also described herein, analytes can be detected accurately using a PSU configured to have both processing regions (e.g., processing regions that generate ultrasonic frequencies (<300 kHz) to lyse cells) and detection regions (e.g., detection regions configured to use graphene-based sensors to detect analytes) even when the detection region is within 2 mm of such a processing region.

In general, one aspect of this document features a device system for detecting the presence, absence, or amount of one or more analytes in a sample, the system comprising at least one assay channel including a graphene sensor and an ASIC electronically connected to the graphene sensor, the ASIC comprising a dedicated analog-to-digital signal processing unit configured to convert raw electronic signals generated by the graphene sensor into digital data that is specifically associated with the assay channel. The system can include a plurality of assay channels. The plurality of assay channels can include from about 128 channels to 256 channels. The graphene sensor can be functionalized with one or more biological probes. The ASIC can be configured to control one or more processing steps to be performed within a processing region of the assay channel. The ASIC can include multiple independent and dedicated signal processing paths. Each signal processing path can include a positive and negative terminal that are electrically connected to the corresponding graphene sensor in the assay channel. Each analog-to-digital signal processing unit can include a signal amplifier, an ADC, a digital filter, a buffer, and an I/O interface. The assay channel can include an input region configured to receive a portion of the sample inserted into the system, a processing region, and a detection region. The input region can be configured to receive a portion of a sample inserted into the system. The processing region can be configured to prepare components within the sample for detection. The processing region can be a cell lysis region configured to lyse cells within the sample. The detection region can be configured to include the graphene sensor, and the graphene sensor can include a capture agent capable of binding to one or more analytes. The assay channel can include a single-stranded nucleic acid attached to the graphene sensor. The graphene-based sensor can include a capture agent that binds to NS1 polypeptides of a Zika virus. The one or more analytes can include proteins, nucleic acids, intact cells, viruses, intact viruses, microorganisms, intact microorganisms, chemicals, and combination thereof.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting. The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 1A-1D show an exemplary graphene-based sensor system.

FIGS. 2A-2E show another exemplary graphene-based sensor system.

FIGS. 3A-3E show another exemplary graphene-based sensor system.

FIG. 0.11 shows an example ASIC 1100 that can be used to implement the PSUs described herein.

DETAILED DESCRIPTION

Figure 4:
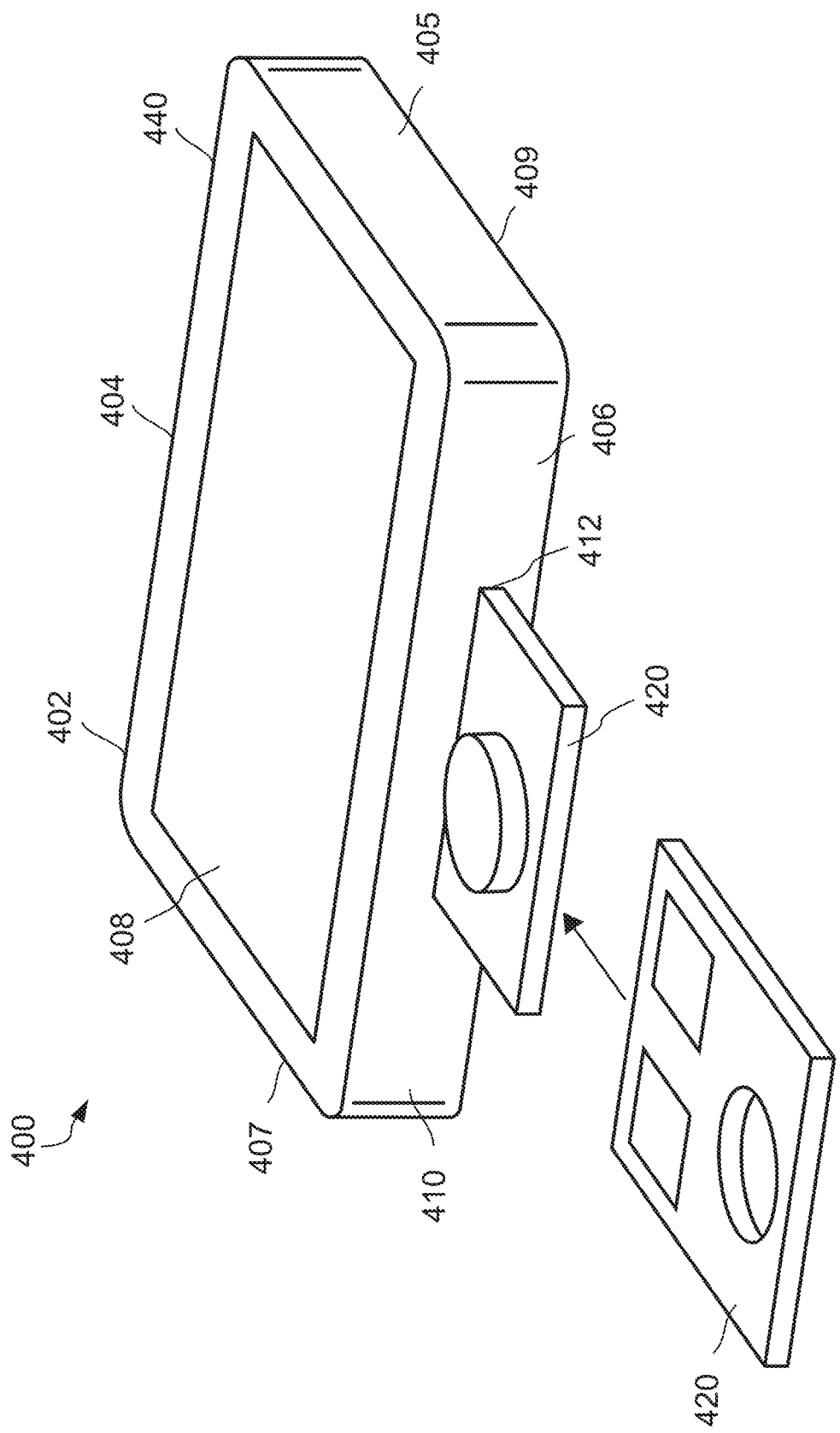
FIG. 4 shows another exemplary graphene-based sensor system.

This document provides methods, devices, and systems for detecting the presence, absence, or amount of one or more analytes (e.g., proteins, nucleic acids, intact cells, intact viruses, intact microorganisms, and/or chemicals) within a sample (e.g., a sample obtained from a patient). For example, this document provides graphene-based sensors to detect one or more analytes within a sample.

In many scenarios, embodiments include one or more graphene sensors that are configured with a single strand of DNA or an antibody, that bind with the corresponding strand of DNA or protein and therefore have a changed resistance. A circuit connected graphene sensor can detect the change in resistance and convert this to a digital signal (typically either an on or off). The graphene sensor is located in a channel such that the sample may flow to it. A device including this may include multiple channels, all testing the same sample that is applied at a point where the channels are joined. Each graphene sensor may test for a different analyte from a sample applied and do so at approximately the same time. In this specification, where it states that measuring occurs "at the same time" or "simultaneously." this may not mean that the measuring/sensing occurs at exactly the same second, but as a result of measuring the same sample of a test, taking into account the context of course.

In some cases, the methods, devices, and systems provided herein can provide reagent-free detection and/or label-free detection of one or more analytes within a sample. For example, graphene-based sensors provided herein can be used in reagent-free and/or label-free diagnostics. Examples of reagents include, without limitation, enzymes, acids, bases, buffers, and detergents. In some cases, methods, devices, and systems provided herein can provide culturefree detection of one or more microorganisms (e.g., infectious microorganisms). For example, a graphene-based sensor provided herein can be used to diagnose infections without requiring an extended period of time to culture the microorganism(s). In some cases, the methods, devices, and systems provided herein can be used in point-of-care applications. The term "point-of-care" as used herein refers to situations where a sample to be analyzed is obtained from a mammal (e.g., obtained from a human such as a human patient) and analyzed such that results of the analysis are provided at or near the location where that mammal can be treated (e.g., a hospital or medical clinic). For example, in healthcare applications, point-of-care can be when a patient sample is analyzed and the results are received at the time of care, e.g., during a doctor's visit. The ability to obtain point-of-care results can allow a doctor and/or patient to make medical treatment or further diagnostic decisions regarding treatment and/or therapy. In some cases, the methods, devices, and systems provided herein can be used by individuals outside the medical/biotechnology profession (e.g., for in-home applications or self-testing applications).

The methods, devices, and systems provided herein can be used in any appropriate application. Examples of applications for which the methods, devices, and systems provided herein can be used include, without limitation, antimicrobial resistance testing, therapy monitoring, biomedical diagnostics (e.g., diagnostics of surgical site infections, bloodstream infections, and/or inflammatory masses), drug screening, environmental contamination assessment, food safety assessments, the development (e.g., discovery) and commercialization of new drugs and/or pharmaceutical compounds.

In some cases, the methods, devices, and systems provided herein can be used to identify the presence of a virus based, at least in part, on the presence, absence, or amount of one or more analytes in a sample. For example, a graphene-based sensor provided herein can be designed for viral diagnostics using one or more capture agents having the ability to bind one or more analytes from infectious viruses. In some cases, a graphene-based sensor provided herein can be designed for environmental contamination assessments and/or food safety assessments using one or more capture agents having the ability to bind one or more analytes from potentially contaminating viruses. Examples of viruses (e.g., potentially infectious viruses and/or potentially contaminating viruses) that can be detected using the methods, devices, and systems provided herein include, without limitation, human immunodeficiency virus (e.g., HIV1 and HIV2), Zika virus, influenza virus A and B, adenovirus 4. RSV, parainfluenza types 1, 2, and 3, human coronaviruses OC43, 229E and HK, human metapneumovirus, rhinoviruses, enteroviruses, hepatitis A, B, C and E viruses, rotavirus, human papillomavirus, measles viruses, caliciviruses, astrovirus, West Nile virus. Ebola virus, Dengue fever virus, African swine fever, herpes simplex virus (e.g., HSV-2). Norwalk and Norwalk-like viruses, enteric adenoviruses, yellow fever virus, chikungunya virus, Epstein-Barr virus, parvovirus, varicella zoster virus, and Ross River virus.

In some cases, the methods, devices, and systems provided herein can be used to identify the presence of a microorganism (e.g., bacteria, fungi, and protozoa) based, at least in part, on the presence, absence, or amount of one or more analytes in a sample. For example, a graphene-based sensor provided herein can be designed for microorganism diagnostics using one or more capture agents having the ability to bind one or more analytes from infectious microorganisms. In some cases, a graphene-based sensor provided herein can be designed for environmental contamination assessments and/or food safety assessments using one or more capture agents having the ability to bind to one or more analytes from a contaminating microorganism. In some cases, methods, devices, and systems provided herein can be used to identify the presence of an antimicrobial resistant bacteria (e.g., methicillin-resistant *Staphylococcus aureus* (MRSA) and methicillin-sensitive *S. aureus* (MSSA)). Examples of microorganisms (e.g., potentially infecting microorganisms and/or contaminating microorganisms) that can be detected using the methods, devices, and systems provided herein include, without limitation, bacterial microorganisms such as *Staphylococcus aureus* (e.g., MRSA and MSSA), *Streptococcus pyogenes, Streptococcus pneumoniae, Mycoplasma pneumoniae, Haemophilus influenzae, Chlamydia pneumoniae, Bordetella pertussis, Mycobacterium tuberculosis, E. coli* (e.g., enterohaemorrhagic *E. coli* such as O157:H7 *E. coli* or enteropathogenic *E. coli*), *Salmonella* species (e.g., *Salmonella enterica*). *Listeria monocytogenes, Acinetobacter baumanni, Klebsiella oxytoca, Giardia intestinalis, Sarcoptes scabiei, Neisseria gonorrhoeae. Chlamydia trachomatis. Treponema pallidum, Campylobacter* species (e.g., thermophylic strains of *Campylobacter jejuni, C. lari*, or *C. coli*), *Bacillus cereus, Vibrio* species, *Yersinia enterocolitica, Shigella* species, *Enterococcus* species (e.g., *Enterococcus faecalis* or *E. faecium*), *Helicobacter pylori*, and *Clostridium* species (e.g., *Clostridium botulinum* or *Clostridium perfringens*), fungal microorganisms such as *Aspergillus* species (e.g., *A. flavus, A. fumigatus*, and *A. niger*), yeast (e.g., *Candida norvegensis* and *C. albicans*), *Penicillium* species, *Rhizopus* species, and *Alternaria* species, and protozoan microorganisms such as *Cryptosporidium parvum. Giardia lamblia*, and *Toxoplasma gondii*.

Any appropriate sample can be assessed (e.g., for the presence, absence, or amount of one or more analytes) using the methods, devices, and systems provided herein. In some cases, a sample can be a biological sample. In some cases, a sample can be an environmental sample. A sample can contain one or more analytes (e.g., proteins, nucleic acids, intact cells, intact viruses, intact microorganisms, and/or chemicals). For example, a sample can contain whole cells, cellular fragments. DNA, RNA, and/or proteins. Examples of samples that can be used in the methods, devices, and systems described herein include, without limitation, biological samples (e.g., blood (e.g., whole blood, a blood spot, serum, or plasma) samples, urine samples, saliva samples, mucus samples, sputum samples, bronchial lavage samples, fecal samples, buccal samples, nasal samples, amniotic fluid samples, cerebrospinal fluid samples, synovial fluid samples, pleural fluid samples, pericardial fluid samples, peritoneal fluid samples, urethral samples, cervical samples, genital sore samples, hair samples, and skin samples), environmental samples (e.g., water samples, soil samples, and air samples), food samples (e.g., meat samples, produce samples, or drink samples), plant samples (e.g., leaf samples, root samples, flower samples, stem samples, pollen samples, and seed samples), industrial samples (e.g., air filter samples, samples collected from work stations, samples collected from storage facilities and/or products (e.g., grain silos), and samples collected from transportation machinery (e.g., railroad cars, trucks, or pipelines)). In some cases, the methods, devices, and systems provided herein can retain the sample (e.g., in a PSU described herein) for safe and clean disposal.

A sample to be assessed (e.g., for the presence, absence, or amount of one or more analytes) using the methods, devices, and systems provided herein can be obtained using any appropriate technique. For example, biological samples can be obtained using non-invasive (e.g., swab) techniques or invasive techniques (e.g., venipuncture, finger stick, or biopsy). For example, an environmental sample and/or an industrial sample can be obtained using a surface swab technique. In some cases, a sample can be a liquid sample. A liquid sample can be any appropriate volume. For example, a liquid sample can include from about 10 microliters (p L) to about 10 mL (e.g., from about 10 μL to about 8 mL, from about 10 μL to about 5 mL, from about 10 μL to about 3 mL, from about 10 μL to about 2 mL, from about 10 μL to about 1 mL, from about 10 μL to about 500 μL, from about 10 μL to about 250 μL, from about 10 μL to about 100 μL, from about 10 μL to about 50 μL, from about 25 μL to about 8 mL, from about 50 μL to about 7 mL, from about 100 μL to about 5 mL, from about 250 μL to about 2 mL, from about 500 μL to about 1 mL, from about 25 μL to about 20 mL, from about 50 μL to about 20 mL, from about 250 μL to about 20 mL, from about 500 μL to about 20 mL, from about 1 mL to about 20 mL, from about 5 mL to about 20 mL, from about 10 mL to about 20 mL, from about 15 mL to about 20 mL).

A sample to be assessed (e.g., for the presence, absence, or amount of one or more analytes) using the methods, devices, and systems provided herein can be obtained from any appropriate animal. In some cases, a sample to be assessed as described herein can be obtained from a mammal (e.g., a human). Examples of mammals that samples can be obtained from include, without limitation, primates (e.g., humans and monkeys), dogs, cats, horses, cows, pigs, sheep, rabbits, and rodents (e.g., mice and rats). Other examples of animals that samples can be obtained from include, without limitation, fish, avian species (e.g., chickens, turkeys, ostrich, emus, cranes, and falcons) and non-mammalian animals (e.g., mollusks, frogs, lizards, snakes, and insects).

A sample to be assessed (e.g., for the presence, absence, or amount of one or more analytes) using the methods, devices, and systems provided herein can be obtained from any appropriate plant. In some cases, a sample to be assessed as described herein can be obtained from a crop plant (e.g., corn). Examples of plants include, without limitation, corn, soybeans, wheat, rice, trees, flowers, shrubs, grains, grasses, legumes, and fruits.

In some cases, a sample to be inserted into a PSU described herein can be obtained from a source (e.g., a mammal or surface) and directly inserted into the PSU without being pre-processed. For example, a blood sample can be obtained from a mammal (e.g., a human) and directly inserted into a PSU without being pre-processed (e.g., without being treated or manipulated in any way).

In some cases, a sample to be inserted into a PSU described herein can be obtained from a source (e.g., a mammal or surface) and processed prior to being inserted into the PSU (e.g., can be pre-processed). Samples that are pre-processed can be pre-processed using one or more appropriate reagents (e.g., enzymes, acids, bases, buffers, detergents, anticoagulants, and/or aptamers) and/or techniques (e.g., purification techniques, centrifugation techniques, amplification techniques, culturing techniques, and/or denaturing techniques). For example, a blood sample can be obtained from a mammal (e.g., a human) and treated with one or more anticoagulants. Examples of anticoagulants that can be used to pre-process a sample (e.g., a blood sample) include, without limitation. EDTA, citrate (trisodium citrate), heparinates (e.g., sodium, lithium, or ammonium salt of heparin or calcium-titrated heparin), and hirudin. In some cases, a sample (e.g., a sample suspected to contain a microorganism) to be inserted into a PSU described herein can be obtained from a source (e.g., a food preparation surface) and pre-processed by culturing the sample with appropriate culture media for a period of time (e.g., 4 hours to 24 hours) prior to being inserted into the PSU. Examples of other pre-processing techniques that can be performed prior to inserting the sample into a PSU provided herein include, without limitation, centrifugation to obtain cell-containing material, centrifugation to obtain cell-free material, filtration remove cell containing material, cell lysis, nucleic acid purification, protein purification, nucleic acid amplification (e.g., polymerase chain reaction (PCR)), reverse transcription to obtain cDNA, reverse transcription PCR, nucleic acid denaturation, and isothermal amplification.

In some cases, a sample does not require any processing after being inserted into a PSU described herein. For example, a sample (e.g., a sample without any pre-processing or a sample that was pre-processed) can be inserted into a PSU provided herein and directly analyzed via a graphene sensor without any sample processing being performed within the PSU.

In some cases, a PSU described herein can be designed to process a sample (e.g., a sample without any pre-processing or a sample that was pre-processed) after the sample is inserted into the PSU. For example, a sample can be inserted into a PSU described herein, subjected to one or more processing steps within the PSU (e.g., one or more processing steps designed to lyse cells and/or one or more processing steps designed to denature nucleic acid), and analyzed via a graphene sensor within the PSU. Examples for processing a sample within a PSU (e.g., lysing cells within a sample inserted into a PSU) are described in detail herein.

The methods, devices, and systems provided herein can be used to detect any appropriate analyte. Examples of analytes that can be detected as described herein include, without limitation, proteins, nucleic acids, intact cells, viruses (e.g., intact viruses), microorganisms (e.g., intact microorganisms), and chemicals. In some cases, the methods, devices, and systems provided herein can be used to identify an analyte. For example, the methods, devices, and systems provided herein can be used to identify a bacterial analyte or a viral analyte. For example, the methods devices, and systems provided herein can be used to determine whether the analyte is bacterial analyte or a viral analyte.

In cases where an analyte to be detected is a protein, the protein analyte can be any appropriate protein (e.g., mammalian protein, viral protein, bacterial protein, fungal protein, plant protein, or animal protein). In some cases, a protein analyte can be a polypeptide fragment of protein. In some cases, a protein analyte can be an enzyme, receptor, structural protein, immunoglobulin, or cell surface marker. For example, a protein analyte can be a viral protein produced by a cell (e.g., a human cell) that was infected with a particular virus. In some cases, a protein analyte to be detected as described herein can be a protein expressed by a tumor cell (e.g., a tumor marker). In some cases, a protein analyte can include one or more modified amino acids. In some cases, a protein analyte can include one or more post-translational modifications (e.g., phosphorylation, myristoylation, farnesylation, acylation, acetylation, and/or methylation modifications). In some cases, a protein analyte to be detected as described herein can be associated with a disease and/or infection. Examples of proteins that can be detected using the methods, devices, and systems provided herein include, without limitation, prostate specific antigen (PSA), carcinoembryonic antigen (CEA), cancer antigen 125 (CA 125), cancer antigen 15-3 (CA 15-3), alpha-fetoprotein (AFP), hemoglobin, albumin, ferritin, transferrin, haptoglobin, ceruloplasmin, IgA, IgG, IgM, IgE, complement C3, complement C4, fibrinogen, HIV protein p24, penicillin binding protein 2A (PBP2A), troponin, c-reactive protein, procalcitonin, peptide hormones (e.g., follicle-stimulating hormone (FSH), luteinizing hormone (LH), human chorionic gonadotropin (hCG), thyroid stimulating hormone (TSH)), NS1, ENV, interleukins, CD3, CD4, CD47, VP40, human epidermal growth factor receptor 2 (HER2), epidermal growth factor receptor (EGRF), CD10, CD30, and B-Raf. Examples of viral proteins that can be detected as described herein include, without limitation. NS1 polypeptide of Zika viruses to detect Zika virus, NS1 polypeptide of Dengue fever viruses to detect Dengue fever virus, NS1 polypeptide of West Nile viruses to detect West Nile virus, ENV polypeptide of Dengue fever viruses to detect Dengue fever virus. ENV polypeptide of Zika viruses to detect Zika virus. ENV polypeptide of West Nile viruses to detect West Nile virus, ENV polypeptide of Chikungunya viruses to detect Chikungunya virus, and VP40 polypeptide of Ebola viruses to detect Ebola virus.

In cases where an analyte to be detected is a nucleic acid, the nucleic acid analyte can be any appropriate nucleic acid (e.g., mammalian nucleic acid, viral nucleic acid, bacterial nucleic acid, fungal nucleic acid, plant nucleic acid, or animal nucleic acid). A nucleic acid analyte can include DNA. RNA, or a combination thereof (e.g., a DNA/RNA hybrid). In some cases, a nucleic acid analyte can be a single stranded nucleic acid. In some cases, a nucleic acid analyte can be a double stranded nucleic acid. In some cases, a nucleic acid analyte can be a circulating nucleic acid. In some cases, a nucleic acid analyte can be used to identify the presence of an antimicrobial resistant bacteria (e.g., MRSA and MSSA). For example, the methods, devices, and systems provided herein can be used to identify antimicrobial resistance genes (e.g., a *Klebsiella pneumoniae* carbapenemase (KPC) gene, a New Delhi metallo-β-lactamase (NDM) gene, an oxacillinase 48 (OXA48) gene, a methicillin-resistant (mecA) gene, and a vancomycin-resistant (vanA or vanB) gene). In some cases, a nucleic acid analyte can be used in forensic applications (e.g., to compare the identity between samples or to assess a sample's origin). For example, the methods, devices, and systems provided herein can be used to identify a DNA fingerprint and/or detect one or more sex chromosomes. In some cases, a nucleic acid analyte can be associated with a disease and/or infection. For example, a nucleic acid analyte can be a genetic marker (e.g., a nucleic acid mutation such as single nucleotide polymorphisms (SNPs), genome duplications (e.g., gene duplications), genome rearrangements, nucleotide repeats (e.g., triplet repeats such as CAG (cytosine-adenine-guanine) repeats), and genome epigenetic events (e.g., DNA methylation events)). Examples of nucleic acids that can be detected using the methods, devices, and systems provided herein include, without limitation, an X chromosome, a Y chromosome, Zika virus RNA. HIV virus RNA. Epstein-Barr virus DNA, telomeres, a BRCA1 gene, a BRCA2 gene, ABCR genes, a LRRK2 gene, a dystrophin gene, a cystic fibrosis transmembrane conductance regulator (CFTR) gene, a Huntingtin gene, a hemoglobin gene, KPC, NDM, OXA48, mecA, vanA, and vanB.

In cases where an analyte to be detected is a chemical, the chemical analyte can be any appropriate chemical (e.g., vitamin, mineral, hormone, heavy metal, chemical toxin, chemical carcinogen, drug, electrolyte, small molecule, chemical by-product, chemical metabolite, or chemical waste product). For example, particular examples of chemicals that can be detected using the methods, devices, and systems provided herein include, without limitation, glucose, vitamins (e.g., vitamin B12 and folic acid), cholesterol, triglycerides, high density lipoprotein (HDL), low density lipoprotein (LDL), very low density lipoprotein (VLDL), sodium ($Na^+$), potassium ($K^+$), and chloride ($Cl^-$), calcium ($Ca^+$), phosphorus ($PO_4^{-3}$), magnesium ($Mg^{++}$), iron ($Fe^{++}$), lead (Pb), bilirubin (e.g., total bilirubin, direct bilirubin, indirect bilirubin, and neonatal bilirubin), lactic acid, uric acid, creatinine, urea nitrogen (BUN), ammonia ($NH_4^+$), thyroid stimulating hormone (TSH), estrogen, testosterone, beta-human chorionic gonadotropin (beta-HCG), ethanol (alcohol), amphetamines, barbiturates, cannabinoids, opiates, and phencyclidine (PCP).

As described herein, the methods, devices, and systems provided herein can include using one or more capture agents to detect a particular analyte. A capture agent can be any appropriate capture agent. In some cases, a capture agent can have the ability to bind to (e.g., and detect the presence of) an analyte described herein. Examples of capture agents that can be used to bind to and detect an analyte as described herein include, without limitation, antibodies, antigens, binding molecules, nucleic acids, and aptamers.

In some cases, an antibody or antibody fragment can be used as a capture agent to detect the presence, absence, or amount of a protein analyte within a sample being analyzed. For example, a monoclonal antibody, a polyclonal antibody, a bi-specific antibody, a single chain variable fragment (scFv), or an antigen-binding fragment of an antibody (e.g., Fab, Fab', or $F(ab')_2$) can be used to design a PSU having an assay channel for detecting an analyte (e.g., a protein analyte).

In some cases, a protein that binds to another molecule (e.g., another protein or chemical) can be used as a capture agent to detect the presence, absence, or amount of an analyte within a sample being analyzed. For example, a protein antigen (e.g., muscle-specific kinase (MUSK)) can be used as a capture agent to detect the presence, absence, or amount of an immunoglobulin that binds to that protein antigen (e.g., an anti-MUSK autoantibody). In some cases, the presence of anti-MUSK autoantibodies within a human sample can indicate that the human has myasthenia gravis.

In some cases, nucleic acid can be used as a capture agent to detect the presence, absence, or amount of a nucleic acid analyte within a sample being analyzed. Any appropriate nucleic acid can be used as a capture agent to detect the presence, absence, or amount of a nucleic acid analyte within a sample being analyzed. For example, DNA. RNA, and DNA/RNA hybrids can be used as a capture agent. In some cases, a nucleic acid analog (e.g., a peptide nucleic acid (PNA)) can be used as a capture agent to detect the presence, absence, or amount of a nucleic acid analyte within a sample being analyzed. As described herein, a nucleic acid capture agent (or nucleic acid analog capture agent) can be designed to hybridize with a particular nucleic acid analyte. In some cases, a nucleic acid capture agent can be entirely single stranded or can contain at least one or more regions of single stranded nucleic acid. For example, a PSU described herein can include an assay channel that has single-stranded nucleic acid attached to a graphene sensor.

A nucleic acid capture agent described herein (or nucleic acid analog capture agent described herein) can be any appropriate length provided that the capture agent is capable of hybridizing to an analyte to be detected. For example, a nucleic acid capture agent can be from about 10 to about 500 or more nucleotides (e.g., from about 10 to about 400 nucleotides, from about 10 to about 300 nucleotides, from about 10 to about 200 nucleotides, from about 10 to about 100 nucleotides, from about 10 to about 50 nucleotides, from about 10 to about 25 nucleotides, from about 20 to about 500 nucleotides, from about 30 to about 500 nucleotides, from about 40 to about 500 nucleotides, from about 50 to about 500 nucleotides, from about 15 to about 50 nucleotides, from about 15 to about 25 nucleotides, from about 20 to about 50 nucleotides, or from about 18 to about 25 nucleotides) in length.

A nucleic acid capture agent described herein (or a nucleic acid analog capture agent described herein) can be designed such that any appropriate nucleic acid analyte can be detected using nucleic acid sequence databases such as GenBank®. For example, computer-based programs can be used to design particular nucleic acid capture agents that can bind to a portion of a nucleic acid analyte based on sequence hybridization.

Any appropriate method can be used to obtain a capture agent described herein. For example, molecular cloning techniques, chemical nucleic acid synthesis techniques, and/or chemical protein synthesis techniques can be used to obtain a nucleic acid and protein capture agents.

In some cases, the methods, devices, and systems provided herein can be used to assess a sample for the presence of Zika virus. For example, a PSU described herein can include one or more assay channels having a graphene-based sensor that includes a capture agent (e.g., an anti-NS1 antibody) that binds to NS1 polypeptides of a Zika virus. In some cases, a PSU described herein can include one or more assay channels having a graphene-based sensor that includes a capture agent (e.g., single-stranded nucleic acid that hybridizes to NS1-encoding nucleic acid) that binds to Zika virus nucleic acid that encodes an NS1 polypeptide. Detection of one or more analytes of a Zika virus can indicate the presence of Zika virus in the mammal (e.g., human) from whom the sample was obtained.

In some cases, the methods, devices, and systems provided herein can be used to assess a sample for the presence of HIV virus. For example, a PSU described herein can include one or more assay channels having a graphene-based sensor that includes a capture agent (e.g., an anti-HIV antibody) that binds to a polypeptide of an HIV virus (e.g., a p24 antigen). In some cases, a PSU described herein can include one or more assay channels having a graphene-based sensor that includes a capture agent (e.g., single-stranded nucleic acid that hybridizes to an HIV nucleic acid) that binds to HIV nucleic acid. Detection of one or more analytes of HIV can indicate the presence of HIV in the mammal (e.g., human) from whom the sample was obtained.

As described herein, a PSU can be designed to detect the presence, absence, or amount of one or more analytes within a sample. Such a PSU can have designed to have one of a variety of configurations. A PSU provided herein can be incorporated into various system and device configurations, as discussed in following sections.

FIGS. 1A-1D show an example graphene-based sensor system 100 configured to detect the presence, absence, or amount of one or more analytes. For example, system 100 can detect one or more analytes (e.g., proteins, nucleic acids, intact cells, intact viruses, intact microorganisms, and/or chemicals). System 100 includes a PSU 120 (which can also be referred to as a card or chip) and a MSU 140 configured for coupling to and receiving PSU 120. PSU 120 can be designed to be a self-contained unit capable of receiving a sample (e.g., a biological sample), docking into MCU 140, performing processing steps designed to prepare the sample or components within the sample for detection, generating raw electronic signals related to the presence, absence, or amount of one or more analytes in the sample (e.g., processed sample) via a sensor (e.g., a graphene-based sensor), converting the raw electronic signals into raw digital data, sending the raw digital data related to the presence, absence, or amount of one or more analytes in the sample to the MCU 140, and/or retaining the received sample for safe and clean disposal. In some cases, as shown in FIGS. 1A-1D, PSU 140 can be designed to include a thin rectangular body, having a height from about 2 mm to about 8 mm, a length from about 70 mm to about 80 mm, and a depth from about 20 mm to about 30 30 mm. PSU 120 can be attached to or docked into MCU 140 once a sample is inserted into PSU 120.

In various cases, MCU 140 provided herein can be a portable, hand-held unit capable of receiving PSU 120 containing a sample to be analyzed. MCU 140 can include a housing body 102 including a rectangular-shaped enclosure having first, second, third, and fourth side portions 104, 105, 106, 107 that define outer side walls of system 100, and first and second major planar faces 108, 109 integrally formed with side portions 104, 105, 106, 107. A rectangular enclosure allows components of system 100 to be accommodated within housing 110 and enclosed between front and back major planar faces 108, 109. In other exemplary embodiments, one or more side portions 104, 105, 106, 107 and/or major planar faces 108, 109 may be formed separately and subsequently joined together (e.g., with one or more adhesives, welds, snap-fit connectors, fasteners, etc.).

Housing body 102 includes a displaying portion 110 and a receiving portion 112 on front planar face 108 of the body 102. Displaying portion 110 is configured for communicating information about the presence, absence, or amount of one or more analytes in the sample to a user or other person directly from the MCU 140. Receiving portion 112 can be coupleable to PSU 120 such that PSU 120 can be securely coupled to or released from MSU 140. In some cases, as shown in FIGS. 1A-1C, receiving portion 112 includes a slot-shaped recess shaped and sized to receive PSU 120. Receiving portion 112 can be positioned near or at third side portion 106 of the body 102 while the displaying portion is positioned near or at the first, second, and fourth side portions 104, 105, 107.

In some cases, MSU 140 can also be configured to provide power to the received PSU 120, receiving digital data (e.g., raw digital data) from the PSU 120, processing the received digital data received from the PSU 120 to determine the presence, absence, or amount of one or more analytes in the sample, and/or transmitting information about the presence, absence, or amount of one or more analytes in the sample over a network (e.g., LAN, WAN. BLUETOOTH network, wireless network, wired network, mobile data network, internet, and/or combinations thereof) to a server system (e.g., cloud-based server) and/or another electronic device (e.g., smartphone, laptop computer, or desktop computer). In some cases, MCU 140 provided here can be designed to have a height from about 12 cm to about 20 cm, a length from about 60 cm to about 70 cm, and a depth from about 135 cm to about 140 cm.

Once PSU 120 is attached to MCU 140, the sample can be processed within PSU 120 to prepare the sample or components within the sample for detection. For example, a sample containing cells can be subjected to one or more cell lysis procedures within PSU 120 itself to prepare cellular components such as nucleic acid for detection, as will be discussed further in subsequent figures herein. PSU 120 can generate raw electronic signals based on the binding (or lack thereof) of an analyte of interest to an immobilized capture agent. Raw digital data related to the raw electronic signals generated by a graphene-based sensor contained in PSU 120 can be sent or transmitted to MCU 140. In some cases, raw digital data can be sent from PSU 120 to MCU 140 without being analyzed to determine if the raw digital data are indicative of the presence, absence, or amount of the analyte being assessed.

After MCU 140 receives raw digital data from PSU 120, in some cases. MCU 140 can process the received raw digital data to determine if the raw digital data is indicative of the presence or absence of one or more analytes in the sample. For example, MCU 140 can assess the nature (e.g., the frequency, strength, time sequence, and/or signatures) of particular received raw digital data over time to determine that an analyte was present within the sample. In some cases, MCU 140 can process the received raw digital data in a manner that determines that an analyte of interest is not present within the sample based on minimal changes, or a lack of any changes, in the raw digital data over the time of the sample analysis. In some cases. MCU 140 can process the received raw digital data to determine the amount of one or more analytes in the sample. For example, the MCU 140 can assess the nature (e.g., the frequency, strength, time sequence, and/or signatures) of particular received raw digital data over time to determine that a particular amount of an analyte of interest is present within the sample.

After MCU 140 processes raw digital data received from PSU 120 to determine the presence, absence, or amount of one or more analytes in the sample, MCU 140 can communicate information about the presence, absence, or amount of one or more analytes in the sample to a user or other person directly from MCU 140. For example, MCU 140 can include a display unit and can display information about the presence, absence, or amount of one or more analytes in the sample to a user or other person directly via the display unit. In some cases. MCU 140 can transmit information about the presence, absence, or amount of one or more analytes in the sample over a network (e.g., LAN, WAN, BLUETOOTH network, wireless network, wired network, mobile data network, internet, and/or combinations thereof) to a server (e.g., cloud-based server), or another electronic device (e.g., smartphone, laptop computer, or desktop computer). For example, MCU 140 can include a wireless communication transmitter (e.g., a radio transmitter such as a BLUETOOTH transmitter, a Wi-Fi transmitter, and/or an NFC transmitter, a mobile data network transmitter) and can transmit information about the presence, absence, or amount of one or more analytes in the sample over a network (e.g., LAN, WAN. BLUETOOTH network, wireless network, wired network, mobile data network, internet, and/or combinations thereof) to a server (e.g., cloud-based server) and/or another electronic device (e.g., a user's smartphone). In some cases, an MCU can be configured to (a) communicate information about the presence, absence, or amount of one or more analytes in the sample to a user or other person directly from the MCU only, (b) transmit information about the presence, absence, or amount of one or more analytes in the sample to a network, server, or another electronic device only, or (c) both communicate information about the presence, absence, or amount of one or more analytes in the sample to a user or other person directly from MCU 140 and transmit information about the presence, absence, or amount of one or more analytes in the sample to a network, server, or another electronic device.

In some cases, the processing of raw digital data to determine the presence, absence, or amount of one or more analytes in the sample can be performed by the PCU 120. For example, the ASIC(s) and/or controller/processing unit(s) on the PCU 120 can be programmed to determine the presence, absence, or amount of one or more analytes in the sample, which can be transmitted to the MCU 140.

In some cases, the processing of raw digital data to determine the presence, absence, or amount of one or more analytes in the sample can be performed by a computing device and/or system that is different from the PCU 120 and the MCU 140. For example, the raw digital data can be transmitted from the PCU 120 to the MCU 140, and then retransmitted from the MCU 140 to another device/system, such as a mobile computing device that is communicatively connected to the MCU 140 (e.g., BLUETOOTH network connection, Wi-Fi Direct connection, NFC connection, connection over LAN), a remote server system (e.g., cloud computing server system), and/or other appropriate computing device. In such instances, processing of the raw digital data to determine the presence, absence, or amount of one or more analytes in the sample can be offloaded from the PCU 120 and the MCU 140 to such another computing device/system, which may have greater processing capacity (e.g., larger number of processing units, faster processors, more memory) to more quickly determine the presence, absence, or amount of one or more analytes in the sample.

Other cases for the device/system that determines the presence, absence, or amount of one or more analytes in the sample are also possible, including cases in which the determination is performed across combinations and subcombinations of the PCU 120, the MCU 140, and other computing devices/systems. For example, the MCU 140 can be programmed to perform a portion of the raw digital data processing and a remote server system can be programmed to perform another portion of the raw digital data processing, which can be combined to determine the presence, absence, or amount of one or more analytes in the sample. Other configurations are also possible.

FIGS. 2A-2E show another example graphene-based sensor system 200 configured to detect the presence, absence, or amount of one or more analytes. Similar to the system shown in FIGS. 1A-1D, system 200 can detect one or more analytes (e.g., proteins, nucleic acids, intact cells, intact viruses, intact microorganisms, and/or chemicals).

As best shown in FIGS. 2D and 2E, system 200 includes a PSU 220 and a MSU 240 configured for coupling to and receiving PSU 220. PSU 220 can be designed to be a self-contained unit capable of receiving a sample (e.g., a biological sample), docking into MCU 240, performing processing steps designed to prepare the sample or components within the sample for detection, generating raw electronic signals related to the presence, absence, or amount of one or more analytes in the sample (e.g., processed sample) via a sensor (e.g., a graphene-based sensor), converting the raw electronic signals into raw digital data, sending the raw digital data related to the presence, absence, or amount of one or more analytes in the sample to the MCU 240, and/or retaining the received sample for safe and clean disposal. In some cases, as best shown in FIG. 2D, PSU 240 can be designed to include a thin rectangular body, having a height from about 2 mm to about 8 mm, a length from about 70 mm to about 80 mm, and a depth from about 20 mm to about 30 mm. PSU 220 can be attached to or docked into MCU 240 once a sample is inserted into PSU 220.

In various cases, MCU 240 provided herein can be a portable, hand-held unit capable of receiving PSU 220 containing a sample to be analyzed. MCU 240 includes a housing body 202 having first, second, third, and fourth side portions 204, 205, 206, 207 that define outer side walls of system 200. Housing body 202 also defines first and second major exterior planar faces 208, 209 and first and second major interior planar faces 213, 214 that are integrally formed with side portions 204, 205, 206, 207 to form an enclosure. The enclosure allows components of system 200 to be accommodated within housing 210. In other exemplary embodiments, one or more side portions 204, 205, 206, 207 and/or major planar faces 208, 209, 213, 214 may be formed separately and subsequently joined together (e.g., with one or more adhesives, welds, snap-fit connectors, fasteners, etc.).

System 200 can include many of the same or similar features described for system 100, with exception that housing body 202 includes a rectangular-shaped enclosure having a hinge mechanism that allows a displaying portion 210 and a receiving portion 212 to be visible and accessible when the system is in an open configuration, and overlaid on each other when in a closed configuration. Displaying portion 210 is configured for communicating information about the presence, absence, or amount of one or more analytes in the sample to a user or other person directly from the MCU 240. Receiving portion 212 can be coupleable to PSU 220 such that PSU 220 can be securely coupled to or released from MSU 240. In some cases, as shown in FIG. 2D, receiving portion 212 includes a slot-shaped recess shaped and sized to receive PSU 220. Receiving portion 212 can be positioned on first interior planar face 214 of the body 202 while the displaying portion is positioned on second interior planar face 215 of the body 202.

FIGS. 3A-3E show another example graphene-based sensor system 300 configured to detect the presence, absence, or amount of one or more analytes. Similar to the system shown in FIGS. 1A-1D, system 300 can detect one or more analytes (e.g., proteins, nucleic acids, intact cells, intact viruses, intact microorganisms, and/or chemicals).

As best shown in FIGS. 3D and 3E, system 300 includes a PSU 320 and a MSU 340 configured for coupling to and receiving PSU 320. PSU 320 can be designed to be a self-contained unit capable of receiving a sample (e.g., a biological sample), docking into MCU 340, performing processing steps designed to prepare the sample or components within the sample for detection, generating raw electronic signals related to the presence, absence, or amount of one or more analytes in the sample (e.g., processed sample) via a sensor (e.g., a graphene-based sensor), converting the raw electronic signals into raw digital data, sending the raw digital data related to the presence, absence, or amount of one or more analytes in the sample to the MCU 340, and/or retaining the received sample for safe and clean disposal. In some cases, as best shown in FIG. 3D, PSU 340 can be designed to include a thin rectangular body, having a height from about 2 mm to about 8 mm, a length from about 70 mm to about 80 mm, and a depth from about 20 mm to about 30 mm. PSU 320 can be attached to or docked into MCU 340 once a sample is inserted into PSU 320.

In various cases, MCU 340 provided herein can be a portable, hand-held unit capable of receiving PSU 320 containing a sample to be analyzed. MCU 340 includes a housing body 302 having first, second, third, and fourth side portions 304, 305, 306, 307 that define outer side walls of system 300. Housing body 302 also defines first and second major exterior planar faces 308, 309 and a first major interior planar face 313 that are integrally formed with side portions 304, 305, 306, 307 to form an enclosure. The enclosure allows components of system 30) to be accommodated within housing 310. In other exemplary embodiments, one or more side portions 304, 305, 306, 307 and/or major planar faces 308, 309, 313, 314 may be formed separately and subsequently joined together (e.g., with one or more adhesives, welds, snap-fit connectors, fasteners, etc.).

System 300 can include many of the same or similar features described for system 100, with exception that housing body 302 includes a rectangular-shaped enclosure having a top body portion and a bottom body portion with a slidable mechanism that allows top body portion to slide in a direction coplanar to bottom portion. The slidable mechanism can be configured to allow a displaying portion 310 and a receiving portion 312 to both be visible and accessible when the system is in an open configuration, and for receiving portion 312 to be overlaid over receiving portion 312 when the system 300 in a closed configuration. Displaying portion 310 is configured for communicating information about the presence, absence, or amount of one or more analytes in the sample to a user or other person directly from the MCU 340. Receiving portion 312 can be coupleable to PSU 320 such that PSU 320 can be securely coupled to or released from MSU 340. In some cases, as shown in FIG. 3D, receiving portion 312 includes a slot-shaped recess shaped and sized to receive PSU 320. Receiving portion 312 can be positioned on first interior planar face 314 of the body 302 while the displaying portion is positioned on first exterior planar face 315 of the body 302.

FIG. 4 shows an example graphene-based sensor system 400 configured to detect the presence, absence, or amount of one or more analytes. For example, system 400 can detect one or more analytes (e.g., proteins, nucleic acids, intact cells, intact viruses, intact microorganisms, and/or chemicals). System 400 includes a PSU 420 and a MSU 440 configured for coupling to and receiving PSU 420. PSU 420 can be designed to be a self-contained unit capable of receiving a sample (e.g., a biological sample), docking into MCU 440, performing processing steps designed to prepare the sample or components within the sample for detection, generating raw electronic signals related to the presence, absence, or amount of one or more analytes in the sample (e.g., processed sample) via a sensor (e.g., a graphene-based sensor), converting the raw electronic signals into raw digital data, sending the raw digital data related to the presence, absence, or amount of one or more analytes in the sample to the MCU 440, and/or retaining the received sample for safe and clean disposal. In some cases, as shown in FIG. 4, PSU 440 can be designed to include a thin rectangular body, having a height from about 2 mm to about 8 mm, a length from about 70 mm to about 80 mm, and a depth from about 20 mm to about 30 mm. PSU 420 can be attached to or docked into MCU 440 once a sample is inserted into PSU 420.

In various cases. MCU 440 provided herein can be a portable, hand-held unit capable of receiving PSU 420 containing a sample to be analyzed. MCU 440 can include a housing body 402 including a rectangular-shaped enclosure having first, second, third, and fourth side portions 404, 405, 406, 407 that define outer side walls of system 400, and first and second major planar faces 408, 409 integrally formed with side portions 404, 405.406, 407. A rectangular enclosure allows components of system 400 to be accommodated within housing 410 and enclosed between front and back major planar faces 408, 409. In other exemplary embodiments, one or more side portions 404, 405, 406, 407 and/or major planar faces 408, 409 may be formed separately and subsequently joined together (e.g., with one or more adhesives, welds, snap-fit connectors, fasteners, etc.).

Housing body 402 includes a displaying portion 410 on front planar face 108 of the body 102 and a receiving portion 412 along one of the side portions, for example, the third side portion 406. Displaying portion 410 is configured for communicating information about the presence, absence, or amount of one or more analytes in the sample to a user or other person directly from the MCU 440. Receiving portion 412 can be coupleable to PSU 420 such that PSU 420 can be securely coupled to or released from MSU 440. In some cases, as shown in FIG. 4, receiving portion 412 includes a slot-shaped recess shaped and sized to receive PSU 420. Receiving portion 412 can be positioned near or at third side portion 406 of the body 402 while the displaying portion is positioned near or at the first, second, and fourth side portions 404, 405, 407.

In some cases. MSU 440 can also be configured to provide power to the received PSU 420, receiving digital data (e.g., raw digital data) from the PSU 420, processing the received digital data received from the PSU 420 to determine the presence, absence, or amount of one or more analytes in the sample, and/or transmitting information about the presence, absence, or amount of one or more analytes in the sample over a network (e.g., LAN, WAN. BLUETOOTH network, wireless network, wired network, mobile data network, internet, and/or combinations thereof) to a server system (e.g., cloud-based server), or another electronic device (e.g., smartphone, laptop computer, or desktop computer). In some cases, MCU 440 provided here can be designed to have a height from about 12 cm to about 20 cm, a length from about 60 cm to about 70 cm, and a depth from about 135 cm to about 140 cm.

Figure 5:
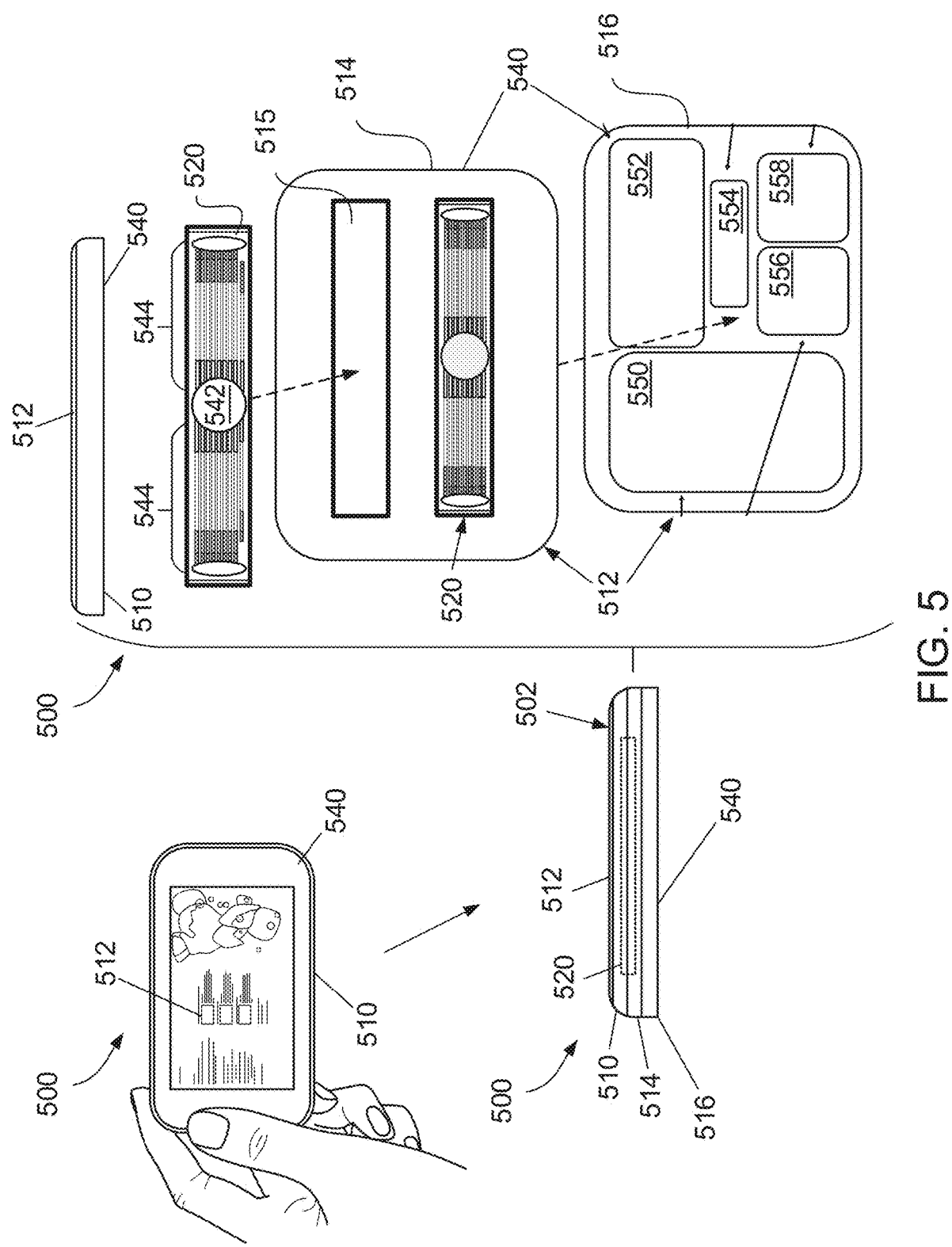
FIG. 5 shows another exemplary graphene-based sensor system.

FIG. 5 shows another exemplary graphene-based sensor system 500 for detecting the presence, absence, or amount of one or more analytes. System 500 can be used to carry out methods for using graphene-based sensors to detect one or more analytes (e.g., proteins, nucleic acids, intact cells, intact viruses, intact microorganisms, and/or chemicals). As depicted, system 500 can be conveniently sized and shaped as a hand-held, portable electronic instrument for point-of-care, molecular diagnostic testing.

System 500 includes a PSU 520 configured for receiving a sample and an MCU 540 configured for receiving PSU 520. PSU 520 provided herein can be designed to be a self-contained unit capable of receiving a sample (e.g., a biological sample) and docking into a master control unit (MCU). MCU 540 can be a portable, hand-held unit capable of receiving PSU 520 and the sample contained therein. MCU 540 can provide power to received PSU 520, receive digital data (e.g., raw digital data) from PSU 520, process the received digital data received from PSU 520 to determine the presence, absence, or amount of one or more analytes in the sample, communicating information about the presence, absence, or amount of one or more analytes in the sample to a user or other person directly from MCU 540, and/or transmitting information about the presence, absence, or amount of one or more analytes in the sample over a network (e.g., LAN, WAN, BLUETOOTH network, wireless network, wired network, mobile data network, internet, and/or combinations thereof) to a server system (e.g., cloud-based server) and/or another electronic device (e.g., smartphone, laptop computer, or desktop computer).

After MCU 540 receives raw digital data from PSU 520 provided herein, MCU 540 can process the received raw digital data to determine if the raw digital data is indicative of the presence or absence of one or more analytes in the sample. For example, MCU 540 can assess the nature (e.g., the frequency, strength, time sequence, and/or signatures) of particular received raw digital data over time to determine that an analyte was present within the sample. In some cases, MCU 540 can process the received raw digital data in a manner that determines that an analyte of interest is not present within the sample based on minimal changes, or a lack of any changes, in the raw digital data over the time of the sample analysis. In some cases, MCU 540 can process the received raw digital data to determine the amount of one or more analytes in the sample. For example, MCU 540 can assess the nature (e.g., the frequency, strength, time sequence, and/or signatures) of particular received raw digital data over time to determine that a particular amount of an analyte of interest is present within the sample.

Once MCU 540 processes raw digital data received from PSU 520 provided herein to determine the presence, absence, or amount of one or more analytes in the sample. MCU 540 can communicate information about the presence, absence, or amount of one or more analytes in the sample to a user or other person directly from MCU 540. For example, MCU 540 can include a display unit and can display information about the presence, absence, or amount of one or more analytes in the sample to a user or other person directly via the display unit. In some cases, MCU 540 can transmit information about the presence, absence, or amount of one or more analytes in the sample over a network (e.g., LAN, WAN, BLUETOOTH network, wireless network, wired network, mobile data network, internet, and/or combinations thereof) to a server (e.g., cloud-based server) and/or another electronic device (e.g., smartphone, laptop computer, or desktop computer). For example, MCU 540 can include a wireless communication transmitter (e.g., a radio transmitter such as a BLUETOOTH transmitter, a Wi-Fi transmitter, an NFC transmitter, and/or a mobile data network transmitter) and can transmit information about the presence, absence, or amount of one or more analytes in the sample over a network (e.g., LAN. WAN, BLUETOOTH network, wireless network, wired network, mobile data network, internet, and/or combinations thereof) to a server (e.g., cloud-based server) and/or another electronic device (e.g., a user's smartphone). In some cases. MCU 540 can be configured to (a) communicate information about the presence, absence, or amount of one or more analytes in the sample to a user or other person directly from MCU 540 only. (b) transmit information about the presence, absence, or amount of one or more analytes in the sample to a network, server, or another electronic device only, or (c) both communicate information about the presence, absence, or amount of one or more analytes in the sample to a user or other person directly from the MCU and transmit information about the presence, absence, or amount of one or more analytes in the sample to a network, server, or another electronic device.

MCU 540 includes a body housing 502 including a cover 510 with a display 512, a receiver 514 (which can also be referred to as an adapter), and a housing base 516, display 512 provide an electronic output showing test analysis results relating to the presence, absence, or amount of one or more analytes. Display 512 can optionally provide a user interface. e.g., a user interface touch screen. Display can be integrated with cover 510, or, in some cases, with any portion of body housing 502.

Receiver 514 of MCU 540 can be coupled to base 516, and positioned between cover 510 and base 516. Receiver 514 includes one or more receiving sites 515 for receiving and electronically coupling to PSU 520. Receiver can be configured to be releasably coupled with PSU 520 to allow a user to load PSU 520 to begin testing, and then later remove the PSU 520 after testing has been completed. In some cases, receiver can include a locking mechanism to securely couple to a PSU that has been inserted into a receiving site 515. Receiver 514 can be configured to electronically connect to electronic components within base 516. Receiver can be made of polymer materials, such as aluminum, metal alloys, and polycarbonates.

Base 516 provides a bottom housing for system 500 and contains various electronic components 550-558 for electronically operating MCU 540. Example electronic components 550-558 can include a power source 550 (e.g., rechargeable battery, solar power unit, electrical connection to an external power source), a system on module 552 (e.g., processors, memory, communication interfaces), a power management subsystem 554 (e.g., separate analog and digital power source management), a mobile data network subsystem 556 (e.g., per-certified module, SIM card interface), and a real-time controller 558 (e.g., feedback control system based on PSU 520 information, such as temperature sensor based control, lysis feedback control). The system on module 552 can include, for example, a system on a chip with one or more processors (e.g., mobile device processors, such as SNAPDRAGON processors), memory (e.g., random access memory (RAM)), short to mid-range wireless communication interfaces (e.g., BLUETOOTH interface, Wi-Fi interface, NFC interface), wired communication interfaces (e.g., USB-C providing power and data), and/or other components. These components 550-558 contained in base 516 (or, in some cases, another portion of MCU 540) can be used to compile biomolecular test results, analyze the test results, and/or communicate the test results to a user. Cover 510 provides a top housing for system 500 and engages with receiver 514 and/or base 516 to protect PSU 520 while PSU 520 is contained within MCU 540, e.g., during the molecular diagnostic testing of sample contained in PSU 520.

PSU 520, as mentioned above, can be configured to receive a sample (e.g., a biological sample) and be docked into MCU 540 to determine the presence, absence, or amount of one or more analytes in the sample, generate raw electronic signals related to the presence, absence, or amount of one or more analytes in the sample (e.g., processed sample) via a sensor (e.g., a graphene-based sensor), convert the raw electronic signals into raw digital data, and/or retain the received sample for safe and clean disposal. PSU 520 can also optionally perform processing steps designed to prepare the sample or components within the sample for detection, and communicate information about the presence, absence, or amount of one or more analytes in the sample to a user or other person directly from MCU 540, and/or transmitting information about the presence, absence, or amount of one or more analytes in the sample over a network (e.g., LAN, WAN, internet, mobile data network, BLUETOOTH network, and/or combinations thereof) to a server system (e.g., cloud-based server) and/or another electronic device (e.g., smartphone, laptop computer, or desktop computer).

PSU 520 can be sized and shaped in various suitable dimensions and geometries. In some cases, PSU 520 provided here can be designed to have a height from about 2 mm to about 8 mm (e.g., about 2 mm to about 6 mm, about 2 mm to about 4 mm, about 2 mm to about 3 mm, about 3 mm to about 8 mm, or about 3 mm to about 6 mm), a length from about 30 mm to about 80 mm (e.g., about 30 mm to about 60 mm, about 30 mm to about 40 mm, about 40 mm to about 80 mm, about 40 mm to about 60 mm, about 40 mm to about 50 mm, about 50 mm to about 80 mm, about 50 mm to about 60 mm, about 60 mm to about 80 mm, about 60 mm to about 70 mm, or about 70 mm to about 80 mm), and a depth from about 15 mm to about 50 mm (e.g., about 20 mm to about 50 mm, about 20 mm to about 40 mm, about 20 mm to about 30 mm, about 30 mm to about 50 mm, about 30 mm to about 40 mm, or about 40 mm to about 50 mm). Once a sample is inserted into PSU 520. PSU 520 can be attached to or docked into MCU 540.

PSU 520, which can be received by and housed within MCU 540, can include a receiving region 542 and assay channels 544. Receiving region 542 of PSU 520 can be configured to receive a biological sample (e.g., blood) from a patient. Assay channels 544 of PSU 520 can be configured to detect the presence, absence, or amount of one or more analytes in the sample. PSU 520 can be a single integral body that includes both receiving region 542 and assay channels 544. In some cases. PSU 520 can include two or more separate, detachable portions. For example, in some cases, PSU 520 can include a first portion that includes receiving region 542, and a second portion that includes assay channels 544. Each respective portion 542, 544 can be coupled to receiver 514.

Receiving region 542 can be configured to receive a biological sample (e.g., blood), or a substrate (e.g., pad or swab) containing the sample. Receiving region 542 can include a circular depressed receiving area where the sample can be placed and temporarily retained for testing. In some cases, receiving region 542 can be configured for receiving and containing a pad or swab containing the sample. In some cases, PSU 520 can include one or more input regions 542 (e.g., one, two, three, four, five, or more than five input regions).

Assay channels 544 includes a set of microfluidic channels to receive a biological sample from receiving region 542, prepare the biological sample for testing (e.g., lyse biological sample), and to test the biological sample for the presence of particular microbiological species. In some cases, PSU 520 can be designed to have one or more assay channels (e.g., 1, 2, 3, 4, 5, 6, 7, 8, 9, 10, 11, 12, or more assay channels). In some cases, assay channels 544 can include more than a hundred microfluidic channels (e.g., 100, 200, 300, 400, 500, or more than 500 microfluidic channels). For example, PSU 520 described herein can be designed to have from about 5 to about 200 assay channels. In some cases, assay channels 544 can include between five to ten, ten to twenty, twenty to thirty, thirty to forty, forty to fifty, or fifty to one hundred assay channels.

Each assay channel 544 can include an input region configured to receive a portion of a sample inserted into PSU 520, a processing region configured to prepare the sample or components within the sample for detection (e.g., a cell lysis region configured to lyse cells within a sample), and a detection region configured to include a sensor (e.g., a graphene-based sensor) having a capture agent capable of binding to an analyte of interest. At the input region, each assay channel fluidically couples with receiving region 542. In some cases, a portion of or all of the assay channel couple to a waste area at a terminal end. At intermediate locations, the biological sample is subject to preconditioning (e.g., lysis) and microbiologically testing. Processing and detection regions will be discussed in greater detail in subsequent sections.

In some cases, the sample inserted into PSU 520, after being processed and analyzed, can be retained within the PSU 520 for safe and clean disposal. For example, PSU 520 provided herein can be a disposable, self-contained unit that is capable of receiving a sample to be assessed and retaining the sample without leakage from the PSU 520 and/or without contaminating other surfaces, components, or people (e.g., without contaminating an MCU used with the PSU).

Figure 6:
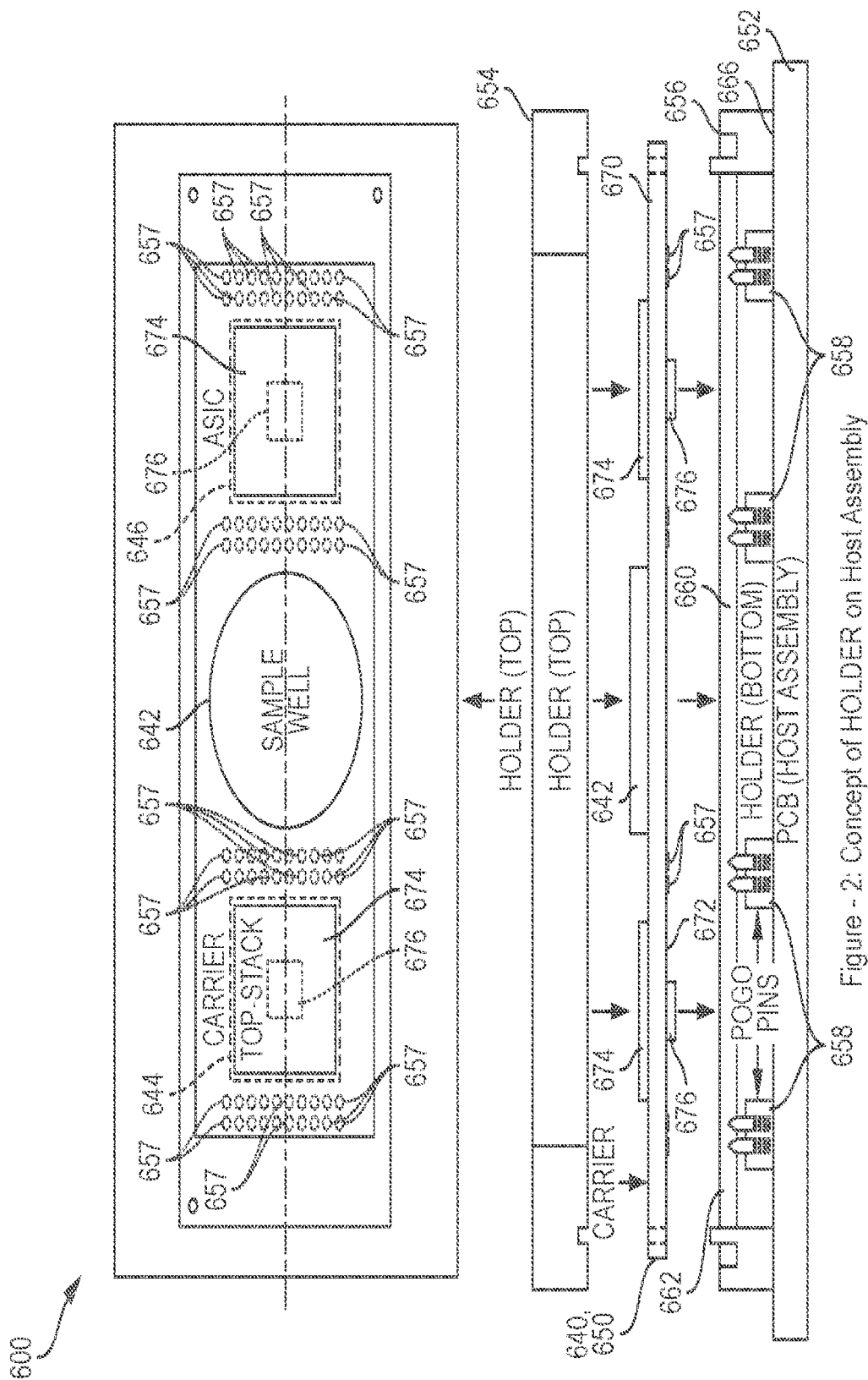
FIG. 6 shows a plan view and an exploded side view of an exemplary processing/sensing unit (PSU).

FIG. 6 shows an example processing/sensing unit (PSU) 600. As depicted, PSU 600 can include a first printed circuit board 650, a second printed circuit board 652, a top housing 654, a bottom housing 656, and a set of electronic connectors 657, 658 (e.g., pogo pin pads) that electronically couple first and second printed circuit boards 650, 652. Top housing 654 is sized and shaped to cover first printed circuit board 650, when top housing 654 is coupled to bottom housing 656. First printed circuit board 650 is disposed on a recessed portion 660 of a first surface 662 of bottom housing 656. A flat second surface 664 of bottom housing 656 is fixedly coupled to a major face 666 of second printed circuit board 652.

First printed circuit board 650 (which can also be referred to as a "carrier substrate") can include a receiving region 642 to receive a biological sample and assay channels 644, 646 for preparing the sample or components within the sample for detection and placing the sample in contact with a sensor (e.g., a graphene-based sensor) to detect the presence, absence, or amount of one or more analytes in the sample. As shown in FIG. 6, first printed circuit board 650 has a first major face 670 that includes one receiving region 642 containing a sample well to receive a biological sample and two assay channel regions 644, 646 containing microfluidic channels (not shown) to test the biological sample. First printed circuit board 650 can include integrated receiving regions 642 and assay channel regions 644, 646 that are fixedly attached to first printed circuit board. In some cases, first printed circuit board 650 can include one or more receiving regions 642 (e.g., one, two, three, four, five, six, seven, eight, nine, ten, or more than ten test sites. In some cases, first printed circuit board 650 can include removable sample wells and/or and assay channels 644, 646 that are releasably attached to first printed circuit board 650.

Each assay channel region 644, 646 of first printed circuit board 650 includes a bare die 674 (with a top stack that can include multiple layers) and an application specific integrated circuit (ASIC) 676. In some cases, the ASIC 676 can have a dedicated analog-to-digital signal processing unit for each assay channel region 644, 646. For example, the ASIC 676 can have multiple dedicated analog-to-digital signal processing units that correspond to the multiple assay channels 644, 646, with each analog-to-digital signal processing unit including a signal amplifier, an analog-to-digital converter (ADC), a digital filter, a buffer, and I/O interface for flushing data stored in the buffer out through one or more busses on the ASIC 676. In some cases, such an ASIC 676 can be designed to control one or more processing steps to be performed within a processing region of a PSU. For example, the ASIC 676 can include a control unit that controls the analog-to-digital processing units and selectively flushes the buffers from each of the analog-to-digital processing units for processing by the PSU, the MSU, a remote computing device/system (e.g., mobile computing device, cloud-based server system), and/or combinations thereof. Die 674 and ASIC 676 are electronically coupled through electrical conductors that extend through first printed circuit board 650. Die 674 can be bonded (e.g., flip-chip bonded) to a first (top) major face 670 of first printed circuit board 650. Each die 674 includes microelectromechanical systems (MEMS) on a first (top) side that are electronically connected by through-silicon-via (TSV) interconnects to electronic connectors on an opposite, second (bottom) side of die 674. ASIC 676 can be bonded to a second (bottom) major face 672 of first printed circuit board 650. An exemplary ASIC 676 can include wafer level chip scale package (WLCSP) ASICs.

Second printed circuit board 652 can include a processor (e.g., Snapdragon 820 processor) and three camera interfaces (e.g., CSI-2 four lane camera interfaces). Second printed circuit board 652 has at least four sets of conductive base connectors 658 (e.g., pogo pin pads) extending from major face 666 of second printed circuit board 652 through bottom housing 656 in a direction generally orthogonal to an X-Y plane that defines major face 666. The connectors 658 electronically connect electronic components (e.g., camera interfaces) of second printed circuit board 652 to the ASIC 676 when connectors 658 extend through bottom housing 658 and come into contact with sensor chip connectors 657 of first printed circuit board 650.

Still referring to FIG. 6, top housing 654 has a rectangular shaped body for securing first printed circuit board 650 between top and bottom housings 654, 656. Top housing 654 optionally defines a rectangular opening to allow a user to view internal components of PSU 640 during testing. Top housing 654 includes a front side, a bottom side, and lateral side walls connecting front and bottom sides. Lateral sides of top housing form walls and a recessed interior for receiving first printed circuit board 650. Lateral sides can include tab openings that mate with tabs of bottom housing 656 to secure top housing 654 to bottom housing 656. Top housing 654 can be shaped in any suitable form, and can be shaped complementary to the shape of first printed circuit board 650. Top housing 654 secures first printed circuit board 650 in place within PSU 620.

Bottom housing 656 has a rectangular shaped body that includes a front side, a bottom side, lateral sides, first surface 662, and a second surface 664. First surface 662 defines a raised perimeter wall and a recessed planar area 660 for receiving first printed circuit board 650. Recessed planar area 660 can be sized and shape to help to align first printed circuit board 650 on bottom housing 656 such that electronic connectors 658 extending from second printed circuit board 652 are aligned with electronic connectors 657 of first printed circuit board 650 when first printed circuit board 650 is placed into recessed planar area 660 of bottom housing 656. Bottom housing 656 provides added structural support for first printed circuit board 650 as well as electronically connect first and second circuit boards 650, 652 together.

Figure 7A:
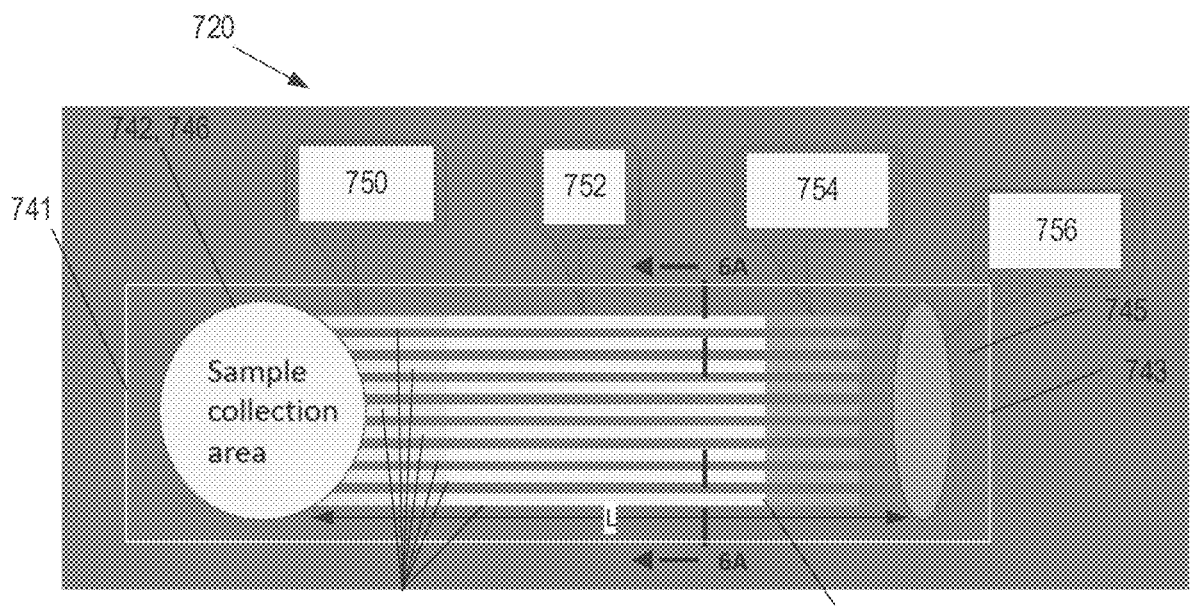
FIG. 7A-7C are plan and side views of an exemplary PSU including a sample collection area and test channels.

FIG. 7A shows an exemplary processing/sensing unit 720 (PSU) for receiving a sample for point-of-care biomolecular testing to detect the presence, absence, or amount of one or more analytes in the sample. PSU 720 includes a receiving region 742 to receive a biological sample and assay channels 744 for preparing the sample or components within the sample for detection and placing the sample in contact with a sensor (e.g., a graphene-based sensor) to detect the presence, absence, or amount of one or more analytes in the sample.

As described herein, each assay channel 744 of PSU 720 described herein can be designed to detect a different analyte. For example, PSU 720 described herein can be designed to have about 100 to 150 assay channels 744, and each detection region of those assay channels can include a sensor (e.g., a graphene-based sensor) having a different capture agent. In some cases, multiple assay channels 744 (e.g., two, three, four, five, or more assay channels) of a single PSU 720 can be designed to detect the same analyte (e.g., protein, nucleic acid, intact cell, intact virus, intact microorganism, or chemical) using either the same capture agent for that analyte or different capture agents for that analyte. For example, two or more different antibodies that have the ability to bind to the same protein can be used is separate assay channels to detect that protein. In such cases, a MCU (e.g., MCU 140 of FIG. 1) can be designed to process the raw digital data for each of those assay channels 744 either separately or as a group to make a determination about the presence, absence, or amount of that protein within the sample.

Referring to FIG. 7A, PSU 720 can include a proximal end 741, a distal end 743, a first major (top) face 745, and a second major (bottom) face 747. PSU 720 can include a receiving region 742 fluidly coupled to assay channels 744 configured for point-of-care biomolecular testing. Receiving region 742 can include assay channels 746 configured for receiving a biological sample (e.g., blood). Assay channels 744 can be a plurality of microfluidic channels 744, in which each assay channel 744 can include an elongated continuous channel containing multiple regions; an input region 750, a processing region 752 (e.g., lysing), and a detection region 754 for detecting the presence, absence, or amount of one or more analytes (e.g., HIV virus) in a sample. Receiving region 742 and assay channels 744 can be made of one or more metals (e.g., stainless steel, nitinol, titanium, platinum, or combinations or alloys thereof), polymers (e.g., polyethylene, polycarbonate, or any copolymers thereof), ceramic materials (e.g., silicon), or combinations thereof.

Receiving region 742 can optionally include a locking mechanism (not shown). For example, in some cases, receiving region 742 includes a rotatable component (not shown) that, when rotated, engages locking mechanism. In some cases, input region 742 can rotate (e.g., 90 degree rotation) to lock input region 742 to an adapter (e.g., see adapter 120 of FIG. 1). In some cases, further rotation (e.g., 180 degree rotation) of receiving region 742 engages a fluidic driver (e.g., a plunger, motor or a piston) to move the biological sample from receiving region 742 to assay channels 744. For example, in some cases, a specific degree of rotation (e.g., 90 degrees) of the rotatable component can remove or open a separation element (not shown), such as a valve, located between receiving region 742 and the assay channels 744.

In use, the biological sample can be deposited into receiving region 742 of PSU 720. Once PSU 720 is placed onto a receiver (e.g., receiving portion 112 of FIG. 1) on a MCU, a component within receiving region 742 can be rotated to engage the locking mechanism such that the sample at receiving region 742 is secured onto the MCU. In some cases, further rotation of one or more components included in receiving region 742 can cause the biological sample to flow into assay channels 744.

Figure 7B:
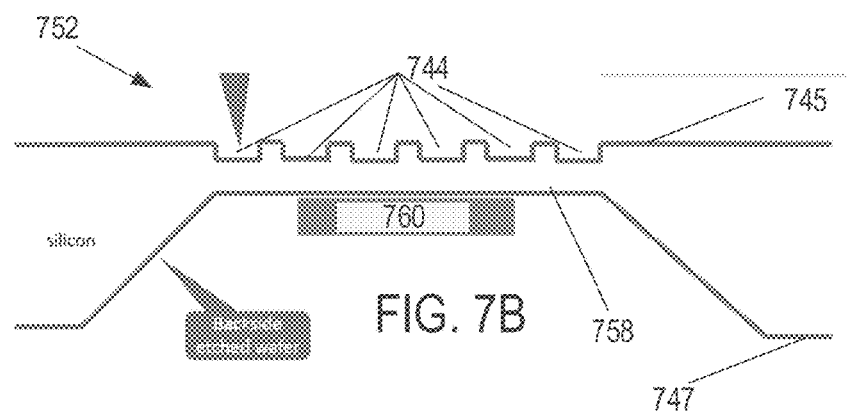
Figure 7C:
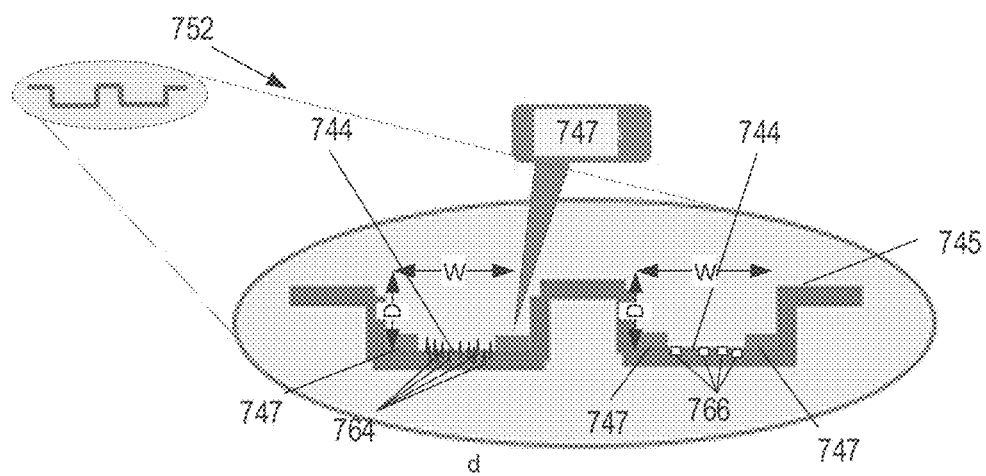

Referring to FIG. 7A, each assay channel 744 extends in a same longitudinal direction. Assay channels 744 of the PSU 720 can have one or more same dimensions (e.g., same length, width, and/or depth). Some or all of the assay channels 744 can have the same cross-sectional shape. For example, each assay channel 744 can the same width "W" and depth "D" (as best shown in FIG. 7C) but different lengths "L" (as best shown in FIG. 7A). In some cases, all of the assay channels 744 can be identical in size and shape. In some cases, one or more of the assay channels 744 can be different in length, width, depth, and/or cross-sectional shape. In some cases, one or more assay channels 744 can extends in a different longitudinal direction (e.g., see FIG. 8). In some cases, the assay channels are dimensioned to obtain equal volume or flow rate among a portion of or all of the assay channels 744. In some cases, the longest dimension of an assay channel 744 of PSU 720 can be less than 10 mm. In some cases, the distance between a processing region 752 (e.g., a cell lysis region configured to lyse cells via, for example, sonication) of one assay channel and a detection region 754 of that same assay channel can be from about 50 μm to about 1 mm. In some cases, analytes can be detected accurately using PSU 720, which has been configured to have both processing regions 752 (e.g., processing regions that generate ultrasonic frequencies (<300 kHz) to lyse cells) and detection regions 754 (e.g., detection regions configured to use graphene-based sensors to detect analytes) even when the detection region 754 is within 1 mm of such a processing region 752.

Referring back to FIG. 7A, each assay channel 744 includes input region 750, processing region 752, and a detection region 754. Input region 750 can be a portion of channel 744 that fluidly couples input region 742 to processing region 752. Input region 750 can optionally include a valve (not shown) that, when open, allows the biological sample to move from input region 742 to processing region 752. When close, the valve prevents the biological sample from entering the assay channels 744 of PSU 720.

Processing region 752 can be a portion of assay channel 744 that extends between input region 750 and detection region 754. After PSU 720 is attached to an MCU, the sample can be processed within PSU 720 to prepare the sample or components within the sample for detection. For example, a sample containing cells can be subjected to one or more cell lysis procedures within PSU 720 itself to prepare cellular components such as nucleic acid for detection. In particular, processing region 752 of PSU 720 can be configured to prepare (e.g. lyse and/or cavitate) the biological sample prior to testing. For example, processing region 752 can be configured to include one or more structures to promote cavitation and/or lysis of the biological sample before the sample passes into detection region 750. Cavitation is the formation of vapor cavities ("bubbles" or "voids") in a liquid when forces act upon the liquid. Subsequent sections will discuss in greater detail the various structures within processing region 752 that promote lysis and cavitation in the biological sample. In some cases, cell lysis can be carried out by using methods described elsewhere, for example, Yen-Heng Lin et al., *An optically induced cell lysis device using dielectrophoresis*, Applied Physics Letters 94, 033901(2009).

In one novel aspect of PSU 720, processing region 752 can include one or more structures configured to perform electro-acoustic lysis on a biological sample. Electro-acoustic lysis, as defined in this document, is a process of lysing a biological species (e.g., a blood cell) when both electrical current and acoustic waves are applied to the biological species. Electro-acoustic lysis provides an advantage of achieving high reliability and probability of lysing the biological sample within processing region 752 within each assay channel 744 before biological sample moves to detection region 754. Referring to FIGS. 7B-7C. PSU 720 can include electrode components 762 within each channel 744 to electrically stimulate the biological sample, and an acoustic generator 760 (e.g., an ultrasound generator) to deliver acoustic waves (e.g., ultrasound) to the biological sample.

As best shown in FIG. 7B, a transverse sectional view of PSU 720 along processing region 752 includes a silicon substrate body etched with multiple channels 744 along top face 745 of PSU 720. At processing region 752, bottom face 747 of PSU 720 defines a cavity 758 configured to receive an ultrasound generator 760. Cavity 758 is positioned vertically below channels 744 such that ultrasound waves generated by an acoustic generator 760 (e.g., an ultrasound generator, an inductive generator, or a radio-frequency (RF) generator) are proximate to and deliver ultrasound waves to the biological sample contained within processing region 752 of PSU 720.

PSU 720 can, in some cases, include a pair of electrodes 762 configured to electrically stimulate the biological sample as the sample passes through processing region 752. Electrodes 762 can extend from a power source positioned proximate to or within an MCU to receiving region 742 to a distal end 768 of processing region 752. Electrodes 762 can include stimulators (not shown) along at least a portion of processing region 752 to target electrical stimulation within processing region 752 only. In some cases, electrodes 762 can include stimulators in one or more regions, e.g., delivery and processing regions 750, 752. Electrodes 762 can be made of one or more metals (e.g., stainless steel, titanium, platinum, or combinations or alloys thereof). Electrodes 762 provide an advantage of delivering electrical current to the biological sample to cavitate and/or lyse biological components within the biological sample, which in turn ensures accurate detection of specific microbiological species contained in the biological sample.

PSU 720 can optionally include other structural features along an interior surface of each channel 744 (e.g., sharp edged needles, pits, and/or pocks) to promote cavitation and/or lysis of biological components within the sample. FIG. 7C shows a magnified transverse sectional view of channels 744 of PSU 720 along processing region 752. Depicted processing region 752 includes sharp edged structures 764, 766 along interior surface of channels 744 configured to promote cavitation and/or lysis of biological components (e.g., cells). Exemplary structures can include sharp protrusions 764 and pits (or cavities) 766 with sharp edges along the walls of each channel 744. In some cases, along its interior surface, each channel 744 can includes sharp protrusions (e.g., needle-like structures 764), an irregular surface, or pits 766 having sharp edges along at least a portion (e.g., top, bottom, and/or side walls) of the channel wall. The sharp protrusions and edges along the walls of the channels 744 can help to weaken, cavitate, and/or lyse the biological sample as the sample passes through processing region 752. In some cases, sharp structural features described herein can be used in combination with electro-acoustic lysis.

In some cases, for example, when intact cell, protein, or microorganisms are evaluated, there may be minimal or no processing step needed to prepare a sample prior to the detection step. As such, in some cases, a PSU (not shown) may not include a processing region 752 such that a sample will immediately move from an input region 750 to a detection region 752. In some cases, a PSU 744 may include one or more assay channels (e.g., 1, 2, 3, 4, 5, 6, 7, 8, 9, 10, half of the channels, a majority of the channels) that do not include a processing region 752.

Referring back to FIG. 7A, assay channels 744 also includes detection region 754, which is configured to detect specific microbiological species (e.g., HIV virus) in a biological sample. Detection region 754 is a portion of assay channel 744 that extends distally from processing region 752. Detection region 754 can include at least one graphene-based sensor configured to chemically interact with the specific analytes. For instance, once the sample is processed in a manner to prepare the sample (or components within the sample) for detection, the sample (or components within the sample) can be placed in contact with a sensor (e.g., a graphene-based sensor) to detect the presence, absence, or amount of one or more analytes in the sample. For example, a sample containing cells can be lysed, and the resulting cell lysis material, which can include cellular nucleic acid, can be contacted with a graphene-based sensor having one or more immobilized (examples of attachment include but are not limited to ionic bonding, pi-pi binding, sigma binding, covalent bonding, polar bonding, electrostatic bonding) capture agents designed to bind to one or more particular nucleic acid analytes that might be present within the sample. Electrical current applied to a graphene-based sensor having one or more immobilized capture agents can generate raw electronic signals based on the binding (or lack thereof) of an analyte of interest to an immobilized capture agent. For example, nucleic acid hybridization of a nucleic acid of interest present within a sample being analyzed to a complementary nucleic acid capture agent attached to a graphene-based sensor present within the PSU can generate raw electronic signals indicative of such hybridization, while the lack of such hybridization can generate raw electronic signals indicative of a lack of such hybridization. In some cases, the raw electronic signals generated within the PSU can be converted into raw digital data within the PSU. For example, a PSU provided herein can include an application-specific integrated circuit (ASIC) designed to detect the generated raw electronic signals and convert them into raw digital data. In some cases, the raw digital data can be sent to the MCU or another device (e.g., cloud-based server system, mobile computing device, laptop, desktop computer, wearable computing device). For example, raw digital data related to the raw electronic signals generated by a graphene-based sensor can be sent or transmitted to the MCU without being analyzed to determine if the raw digital data are indicative of the presence, absence, or amount of the analyte being assessed.

Assay channels 744 can also include a designated area for waste collection after the biological sample has been tested for the presence of specific biological species. For example, some or all of assay channels 744 within assay channels 744 can be fluidly joined together at a waste collection reservoir 756 located proximate the distal end 743 of PSU 720. Alternatively, in some cases, assay channels 744 can each include one or more optional regions, such as a waste collection region, that extends distally from detection region 754.

Figure 8:
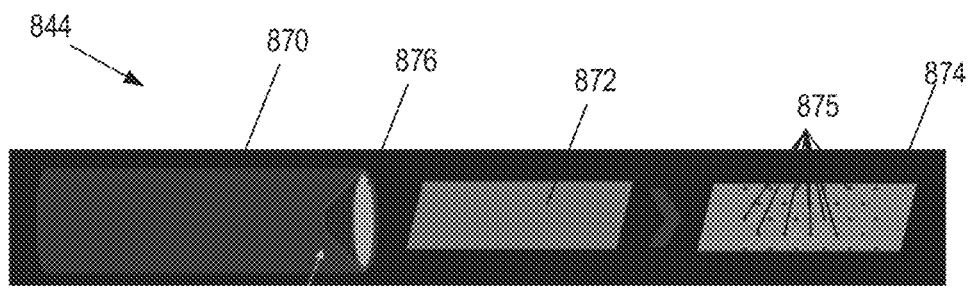
FIG. 8 shows a schematic illustration of components within an exemplary assay channel 844 and components thereof.

FIG. 8 shows a schematic illustration of components within an exemplary assay channel 844. Channel 884 includes a column 870 configured to move a biological sample 872 (e.g., plasma) when subjected to a flow mechanism. An exemplary flow mechanism can include ultrasound-based, pressure driven microfluidics. In some embodiments, channel 884 can optionally include a nozzle 876 (e.g., ribbon nozzle) at one end of the column 870 to transition the sample 872 into a planar film form, and thus changes the sample's columnar-based fluidics to film-based fluidics. In some embodiments, an electrical bias voltage can be applied to the nozzle. The sample can be moved over a portion of the channel 884 that includes graphene sensors 874 functionalized with one or more biological probes 875, as discussed herein. The biological probes can be deposited onto the graphene substrate using methods described elsewhere (see. e.g., Han, *Chem.*, 1:346-348 (2016); Kuang et al., *Biointerphases*, 11:041003 (2016); Kong et al., "Bionic Graphene Nanosensors," in *Carbon Nanonaterials for Biomedical Applications*. Eds: Zhang, Naik, and Dai (Springer, Switzerland, 2016); and Mannoor et al., *Proc. Natl. Acad. Sci. USA* 107:19207-19212 (2010)).

Figure 9A:
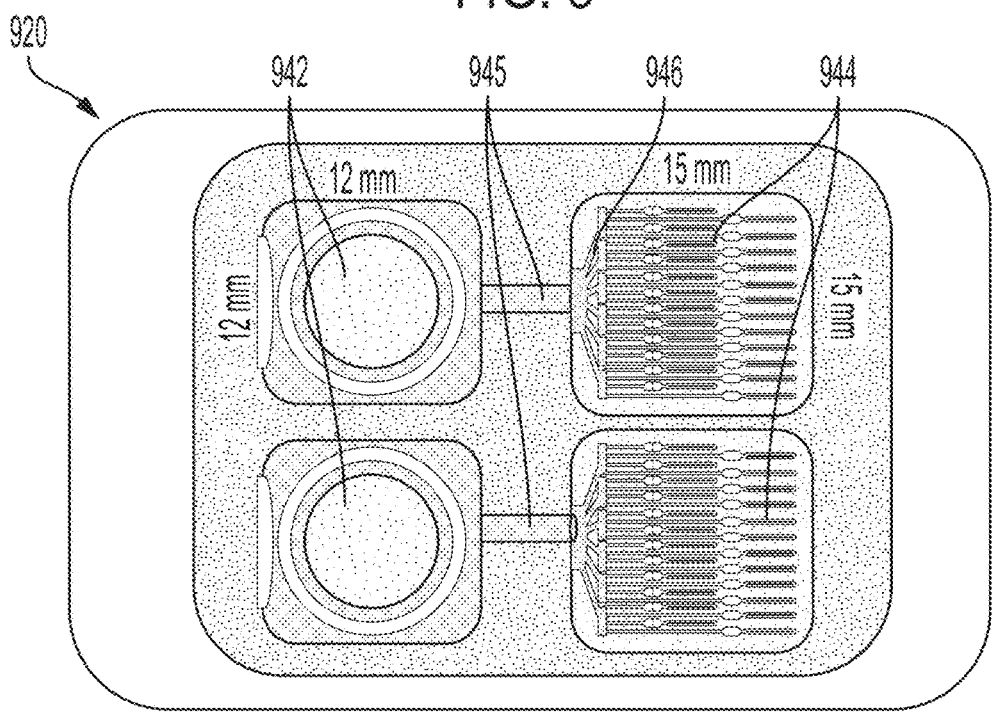
FIGS. 9A and 9B show a plan view of a schematic illustrations of an exemplary PSU and components thereof.
Figure 9B:
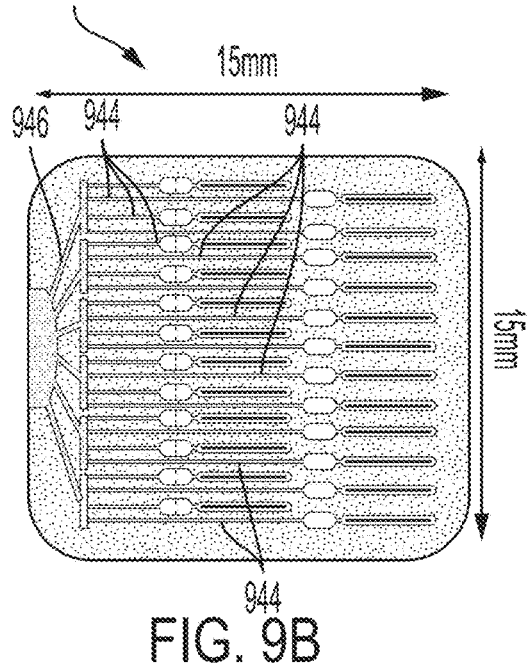

FIGS. 9A and 9B show a plan view of a schematic illustrations of an exemplary PSU 920. PSU 920 can be configured to receive a sample for point-of-care biomolecular testing to detect the presence, absence, or amount of one or more analytes in the sample. PSU 920 includes a receiving region 942 to receive a biological sample and assay channels 944 for preparing the sample or components within the sample for detection by placing the sample in contact with a sensor (e.g., a graphene-based sensor) to detect the presence, absence, or amount of one or more analytes in the sample. PSU 920 can include components and structures similar to or the same as the components and structures associated with PSU 720 (see FIGS. 7A-7C), with the exception of a interconnecting channel 945 that connects receiving portion to assay channels, and the geometry of the assay channels.

Interconnecting channel 945 can be used to help control flow rate and volume of sample being introduced into the assay channels 944. The interconnecting channel 945 can optionally include one or more valves to stop or allow flow of the sample from the receiving region, and into the assay channels 944.

PSU 920 can include a plurality of assay channel 944 that extend in a same or common direction, but have different lengths. In particular, as shown in FIGS. 9A and 9B, an alternating pattern of different channel lengths can be applied to increase space efficiency, and/or to assist with flow rate or volume control. Assay channels 944 of PSU 920 include a common input region 946 for four assay channels. A common input region 946 can help to control and maintain a desired flowrate in the channels.

Figure 10:
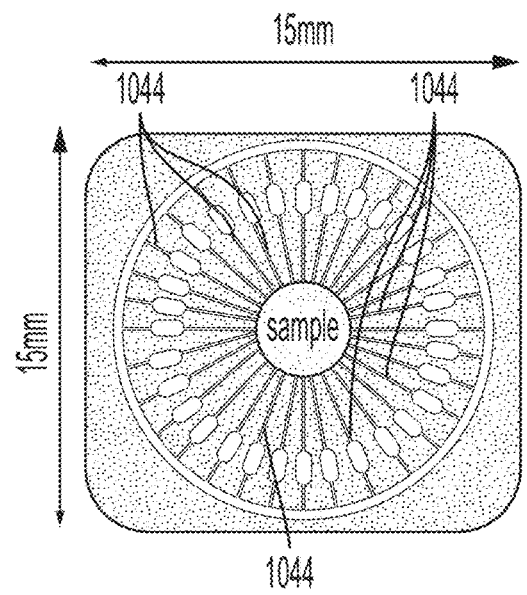
FIG. 10 is a plan view of a schematic illustrations of an exemplary assay channels.

FIG. 10 is a plan view of a schematic illustrations of an exemplary assay channels 1044. Assay channels 1044 can be configured to receive a sample for point-of-care biomolecular testing to detect the presence, absence, or amount of one or more analytes in the sample. Assay channels 1044 can be used to prepare the sample or components within the sample for detection by placing the sample in contact with a sensor (e.g., a graphene-based sensor) to detect the presence, absence, or amount of one or more analytes in the sample. PSU 1020 can include components and structures similar to or the same as the components and structures associated with PSU 720 (see FIGS. 7A-7C), with the exception of the geometry of the assay channels.

As shown, a plurality of assay channel 944 can extend in a radial configuration. A radial pattern can be used to achieve equal distant channel lengths, increase space efficiency, and/or obtain constant flow rate or volume control.

Figure 11:
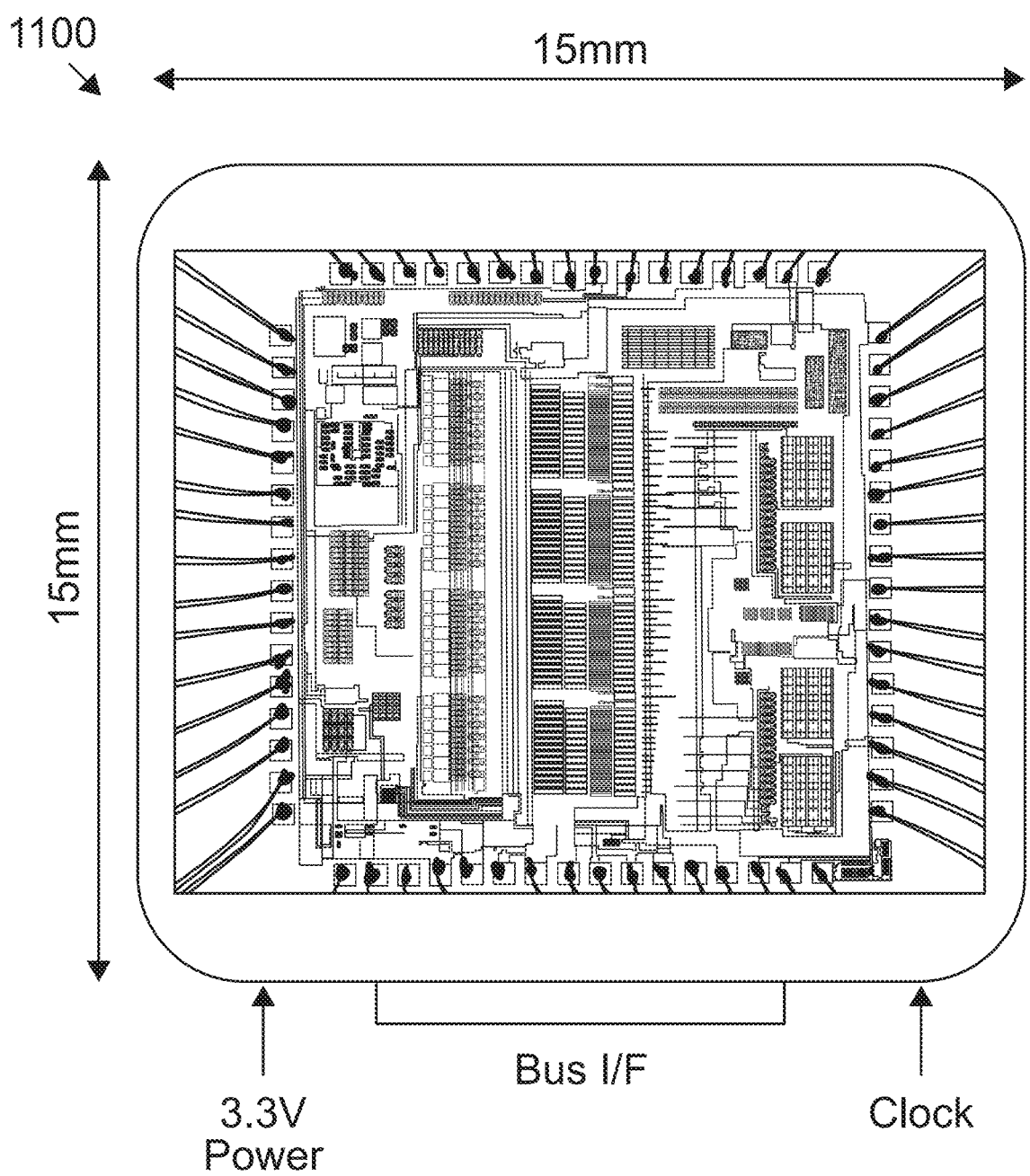

FIG. 11 depicts an example ASIC 1100 that can be used to implement the PSUs described throughout this document. In particular, the ASIC 1100 is depicted as having a form factor of approximately 15 mm by 15 mm, and interfacing with an external device (e.g., controller) to receive power (e.g., 3.3V), to communicate over a bus, and to receive a clock signal. Other implementations of ASICs are also possible.

Figure 12:
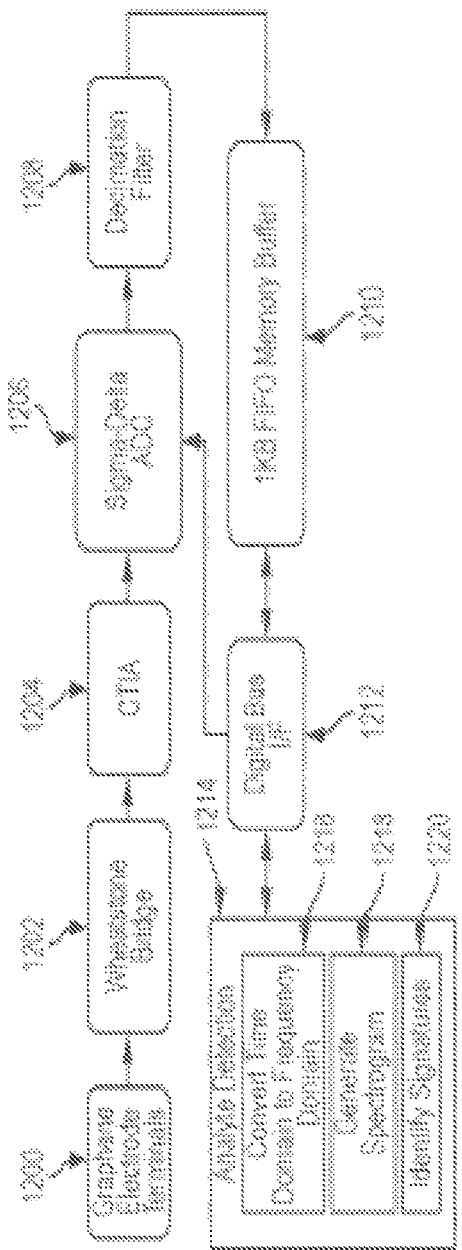
FIG. 12 shows an example analog-to-digital signal processing path.

FIG. 12 depicts an example analog-to-digital signal processing path 1200-1220 for detecting the presence, absence, or amount of one or more analytes in the sample. Some or all of the processing path 1200-1220 can be a dedicated analog-to-digital path that corresponds to a sample channel (e.g., 1:1 ratio between sample channels and analog-to-digital path, 1:M (many) ratio between sample channels and analog-to-digital paths). For example, the portion of the path 1200-1212 can be on an ASIC and can be dedicated to a sample channel-meaning that that the ASIC can include multiple instances of the path 1200-1212 that correspond to the multiple sample channels—and can output raw digital data. The remaining portion 1214-1220 can an analyte detection portion of the path that processes the raw digital data to detect the presence, absence, or amount of one or more analytes in the sample. The analyte detection portion 1214-1220 of the path can be performed by any of a variety of structures, including by one or more of: the ASIC, the PSU, the MSU, connected computing device (e.g., mobile computing device, laptop, wearable computing device), remote computing device/system (e.g., cloud-based computer system), and/or combinations thereof.

In particular, the processing path includes graphene electrode terminals 1200 that are exposed to samples and, as samples bind to sites on the graphene electrode terminals 1200, the resistance and change in resistance across the terminals is measured by a Wheatstone Bridge circuit 1202, which is able to detect resistance and changes in resistance with a high-level of granularity. Analog signals representing the resistance measurements from the Wheatstone Bridge 1202 are passed to an amplifier 1204, which in this example is a capacitance transimpedance amplifier (CTIA), to amplify the analog signals from the Wheatstone Bridge 1202 and to convert capacitance to voltage. These analog signals are then converted to raw digital data by an analog-to-digital converter (ADC) 1206, which in this example is a sigma-delta ADC. The raw digital data is then passed to a filter 1208, which in this example is a decimation filter, to reduce the data sampling rate.

The data is then stored in a memory buffer 1210 (e.g., 1 KB, 2 KB, 4 KB, 8 KB, 16 KB, 32 KB) that is dedicated to buffering raw digital data that is generated from a corresponding channel. For example, as mentioned above, each channel can have a corresponding process path 1200-1212 in the ASIC, which means that there is a raw digital data buffer 1210 dedicated to storing data from the corresponding channel (e.g., if there are 32 channels for taking sample measurements, there can be 32 corresponding paths 1200-1212 with 32 buffers 1210). The raw digital data stored in the buffer 1210 can be flushed periodically through a digital bus interface 1212 that is connected to a digital bus for the ASIC. For example, a controller on the ASIC can sequentially and repeatedly loop through the buffers 1210, sequentially flushing each of the buffers 1210 over the digital bus to retrieve the channel-specific data for subsequent processing. The channel-specific raw digital data can be stored and/or retransmitted by the controller, such as being transmitted to a MCU for processing and analyte detection. Given that the analytes being measured in each channel can vary (e.g., different channels can measure/detect different analytes), the raw digital data that is flushed from the buffer 1210 can be augmented with data identifying the type of channel and/or analyte to which the channel pertains, so that the subsequent data processing to detect the presence, absence, and/or magnitude of analytes can be properly performed.

A variety of advantages can be provided by having a dedicated processing path 1200-1212 for each channel and having the processing path 1200-1202 located on the ASIC near the actual location of the terminals 1200. For example, a distance for signal propagation and conversion to raw digital data can be minimized (as opposed to, for example, transmitting the analog signals to a separate device (e.g., MCU) for digital conversion), which can increase the fidelity and quality of the electrode sensor measurements. In another example, by buffering the raw digital data for each channel, the loss of raw digital data for each channel can be reduced and/or eliminated. In a further example, the complexity of an interface between the ASIC and the PCU and/or MCU can be minimized by permitting raw digital data from all channels to be transmitted over a common bus as opposed to either needing a separate interface corresponding to each channel and/or potentially losing signals by switching across different channels on a common bus. In another example, a larger number of channels can be used and a larger number/wider variety of analytes can be detected simultaneously by permitting multi-channel data collection, storage, and retransmission in a lossless environment.

Analyte detection 1214 can be performed using the raw digital data corresponding to each channel. Any of a variety of appropriate techniques can be used to identify the presence, absence, and/or magnitude of analytes under test in a sample. In one example technique, the raw digital data can be converted from a time domain to a frequency domain (1216). For $$X_k = \Sigma_{n=0}^{N-1} e^{-i2\pi k n/N} \quad k=0, \ldots, N-1$$

example, the sampled signals from all channels (e.g., 32 channels) can be converted into raw digital data that is provided in a time series as an array of data approximately 16-18 bits for each sample and acquired at a rate of 1 MHz. In addition to time-domain data, the time-domain data can be converted into frequency domain data using, for example, a fast fourier transform (FFT) algorithm that is executed on a digital signal processing chip located, for example, in the PCU and/or MCU. For instance, the following equation can be used to convert the data from a time domain into the frequency domain:

The frequency domain data can then be plotted against time to generate a spectrogram (1216), which, when visualized, can depict amplitude at each frequency and each point in time. A spectrogram can be generated for each graphene biosensor channel on the device.

Using the spectrograms, analyte signatures indicating the presence, absence, and/or magnitude of various analytes in the sample can be generated (1220). For example, empirical analysis can be performed on the spectrograms using known samples to generate signature models correlated to the presence, absence, and/or magnitude of analytes in samples. These models get be applied to the spectrograms using various techniques to detect the presence, absence, and/or magnitude of analytes.

Figure 13:
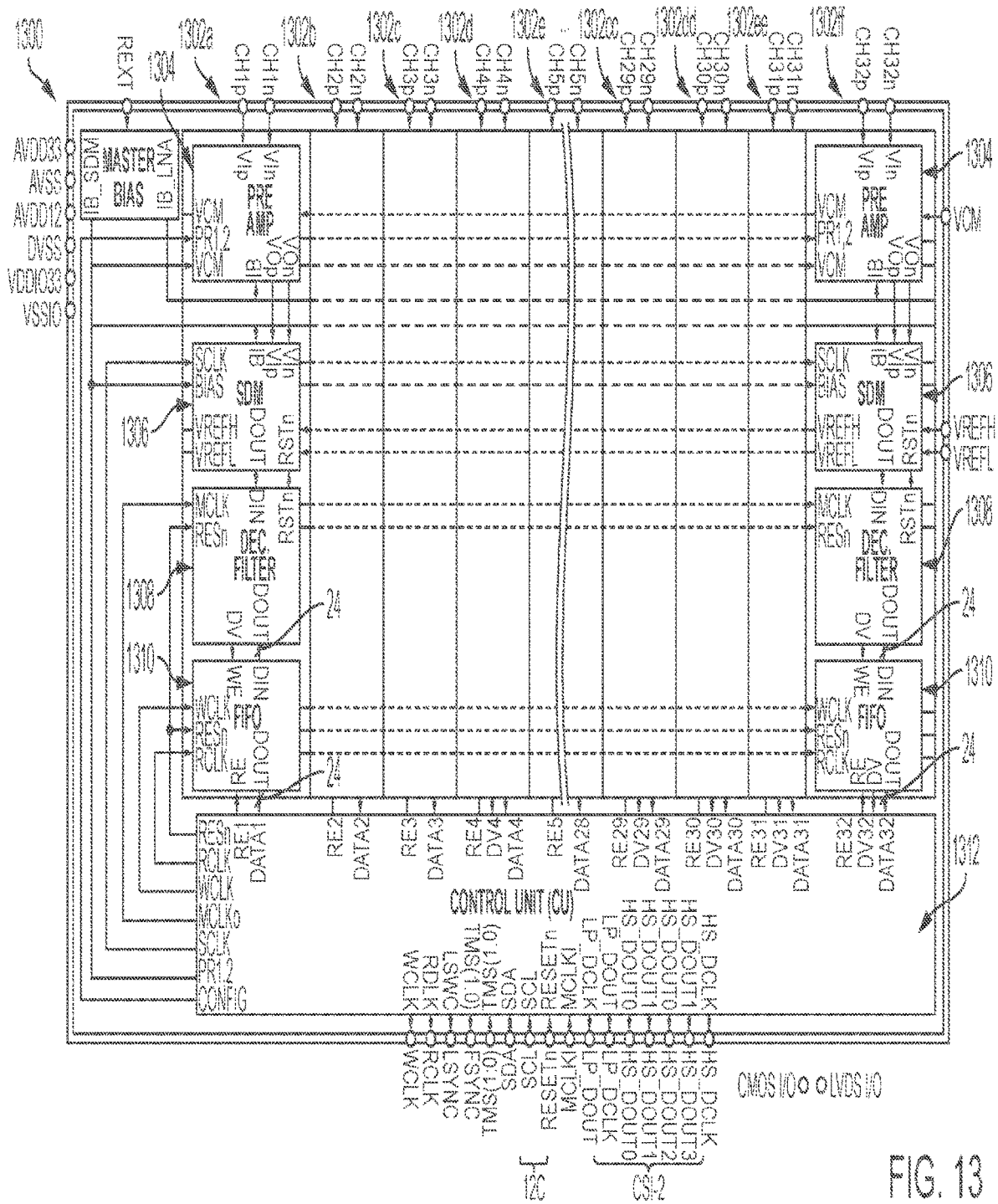
FIG. 13 is a schematic illustration of an architecture overview for an example ASIC.

FIG. 13 is an architecture overview for an example ASIC 1300. The ASIC 1300 depicts example ASIC components 1200-1212 for across multiple different channels. For example, the ASIC 1300 includes multiple independent and dedicated signal processing paths 1302a-ff, which in this example are depicted as 32 channels (other number of channels are also possible). Each signal processing paths 1302a-ff includes a positive and negative terminal (e.g., "CH1p." "CH1n") that are electrically connected to corresponding graphene sensors in each of the channels. Each signal processing paths 1302a-ff also includes a preamplifier 1304 to measure the capacitance across the graphene sensors (similar to 1202), an SDM 1306 to amplify the signal and to convert the signal to raw digital data (similar to 1204-1206), a decimation filter 1308 to adjust the sampling rate (similar to 1208), and a buffer 1310 (similar to 1210).

The ASIC 1300 also includes a control unit 1312 that obtains data from the buffers 1310 for each of the signal processing paths 1302a-ff. The controller 1312 also augments the data from the buffers 1310 for each of the signal processing paths 1302a-ff with information identifying the corresponding channel from which the raw digital data was generated, and includes an interface through which the data is transmitted to a controller on the PCU, MCU, and/or other computing device (e.g., cloud-based server system, mobile computing device).

Figure 14A:
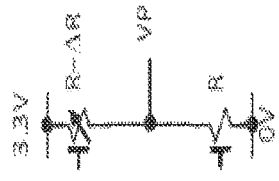
FIGS. 14A-C show example GFET interfaces that can be used to measure resistance from the graphene sensors.
Figure 14B:
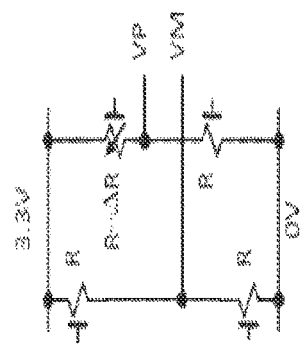
Figure 14C:
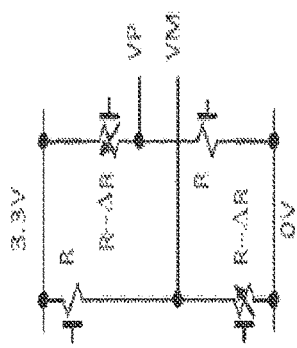

FIGS. 14A-C depict example GFET interfaces that can be used to measure resistance from the graphene sensors. The example GFET interfaces can be implemented as part of, for example, the detection unit 1202 and/or the preamplifier 1304. The example GFET interfaces each generate a signal that is a result of the change in resistance in the GFET, which is a transient response (as opposed to an integrated response). The example GFET interface depicted in FIG. 14A has a dual GFET site with a single active GFET. The example GFET interface depicted in FIG. 14B has a quad GFET site with a single active GFET, and is an example representation of a Wheatstone Bridge. The example GFET interface depicted in FIG. 14C has a dual GFET site with dual active GFETs. The detection unit 1202 and/or the preamplifier 1304 can be implemented using any of these example GFET interfaces in FIGS. 14A-C, and/or can be implemented using other GFET interfaces or detection circuits.

Figure 15A:
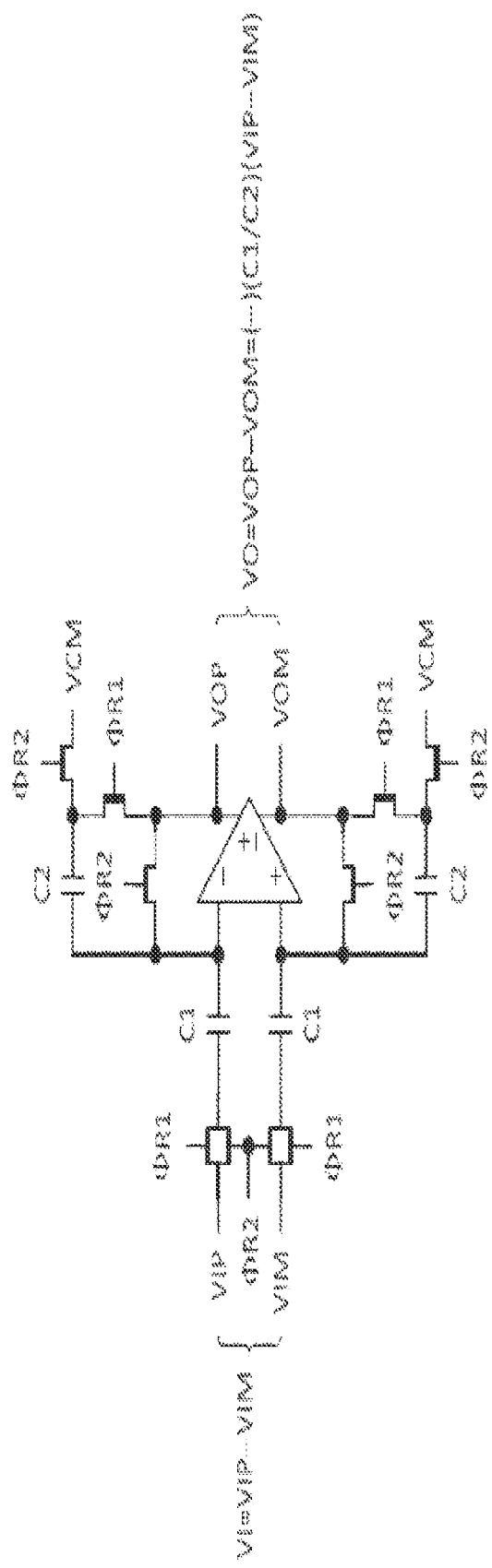
FIGS. 15A-B show an example pre-amplifier circuit and a timing diagram.
Figure 15B:
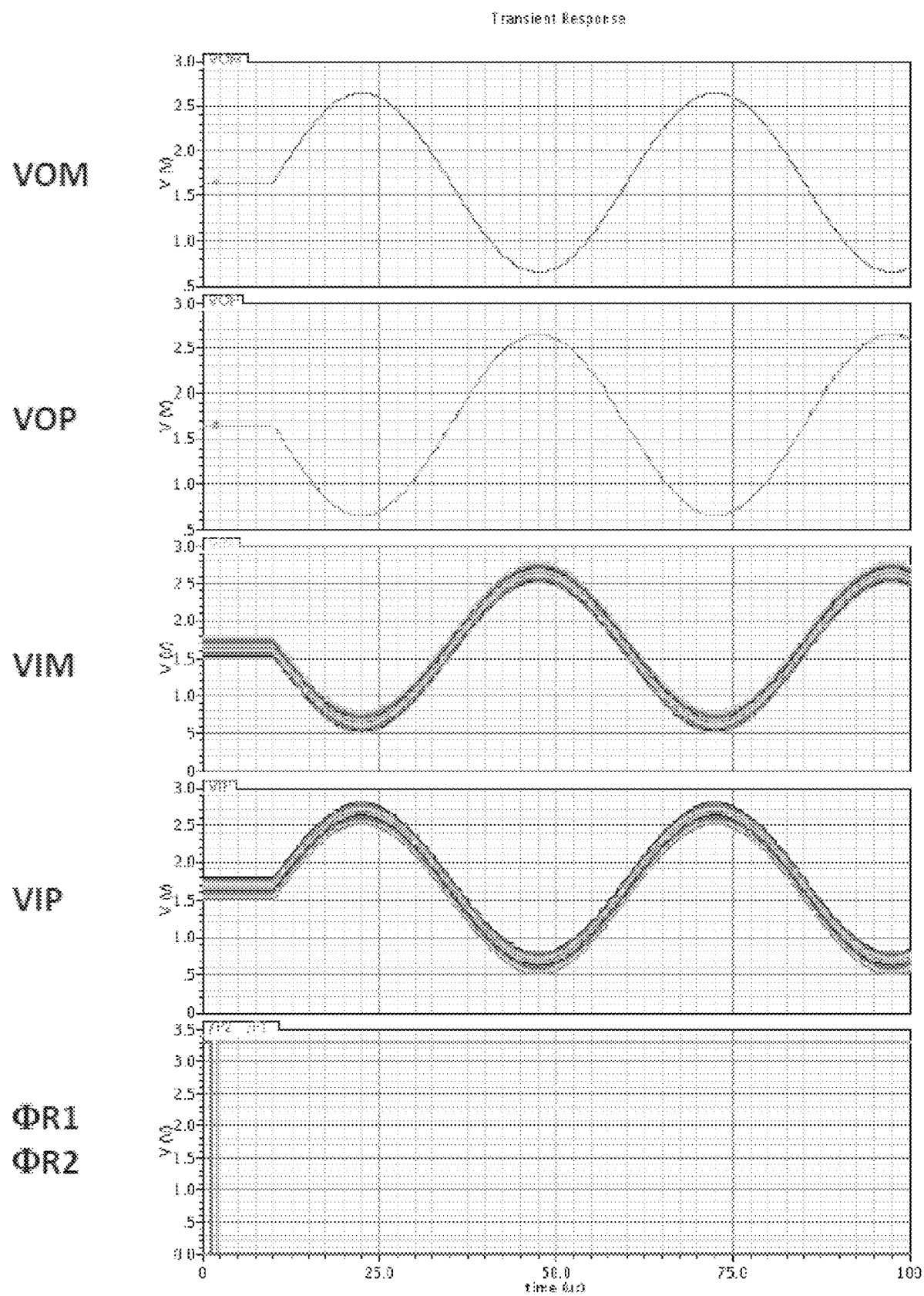

FIGS. 15A-B depict an example pre-amplifier circuit and a timing diagram detailing the transient response of the pre-amplifier circuit. The example circuit depicted in FIG. 15A can be implemented as the CTIA 1204 and as part of the preamplifier 1304. The example circuit removes the GFET interface offset, the preamplifier offset, and any system 1/f noise, and is able to drive the input of the SDM 1206/1306. FIG. 15B is a timing diagram showing the transient response for the circuit depicted in FIG. 15A.

Figure 16A:
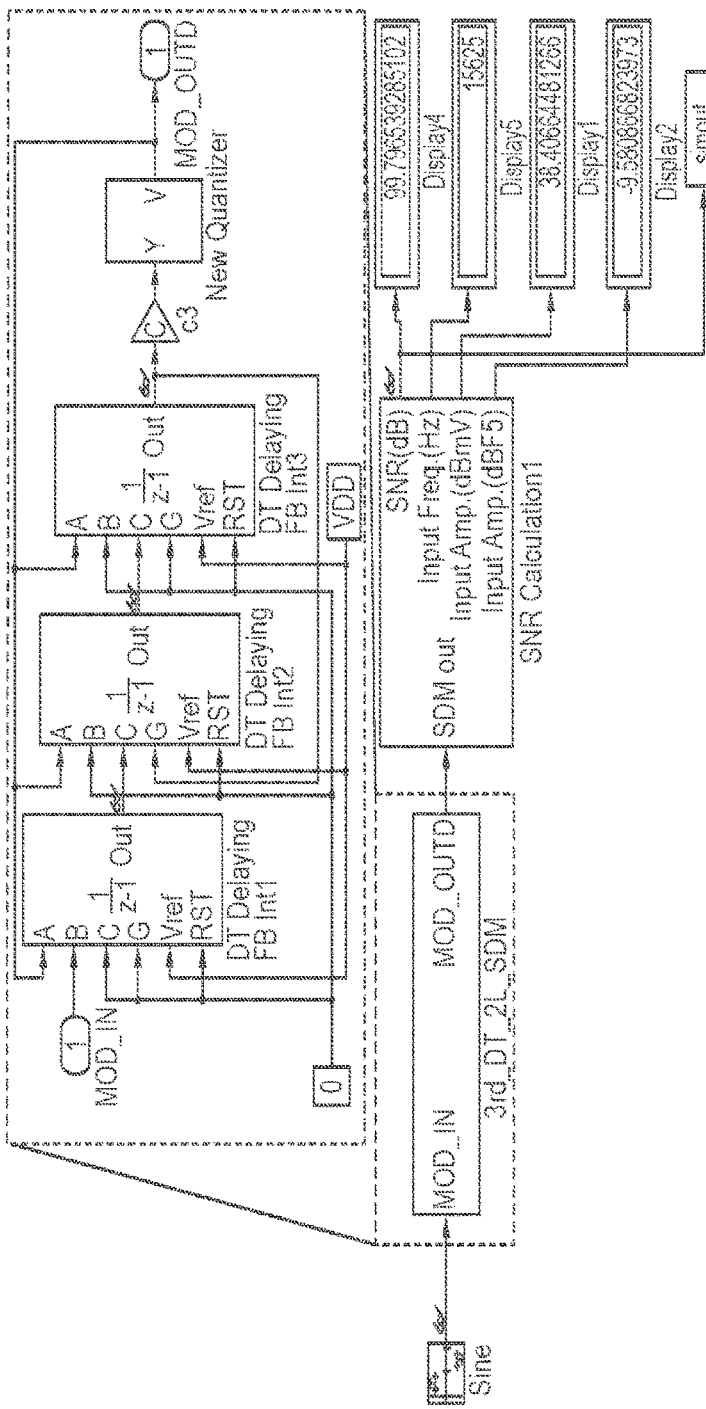
FIGS. 16A-B depict an example SDM circuit and a timing diagram.
Figure 16B:
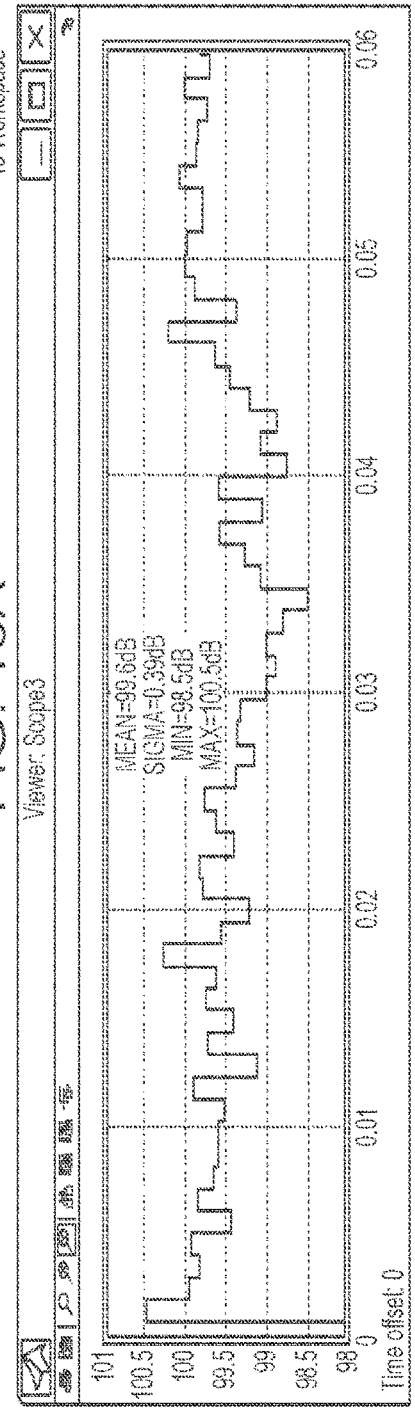

FIGS. 16A-B depict an example SDM circuit and a timing diagram detailing the digital output of the SDM circuit. The example circuit depicted in FIG. 16A can be implemented as the SDA 1206 and as the SDM 1306. The example circuit can operate as an analog-to-digital converter that maximizes the effective number of bits (ENOB) that are output through the circuit (e.g., ENOB of 18*b* or greater). FIG. 16B is a timing diagram showing the digital output for the circuit depicted in FIG. 16A.

Figure 17A:
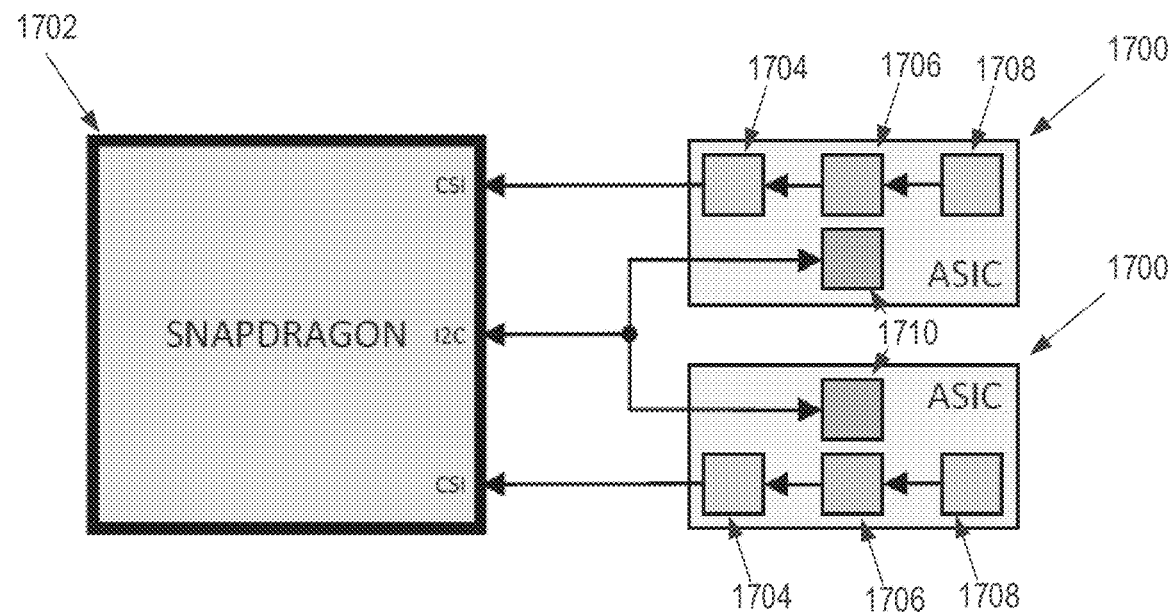
FIGS. 17A-D depict different example implementations for interfacing an ASIC with an example controller for the PCU.
Figure 17B:
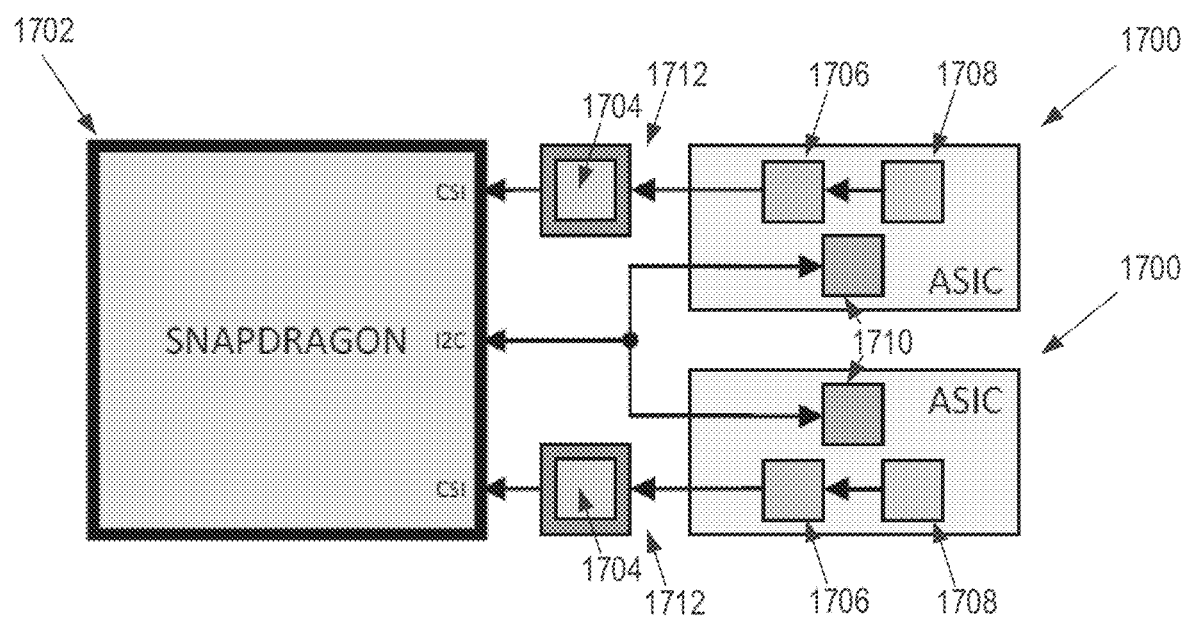
Figure 17C:
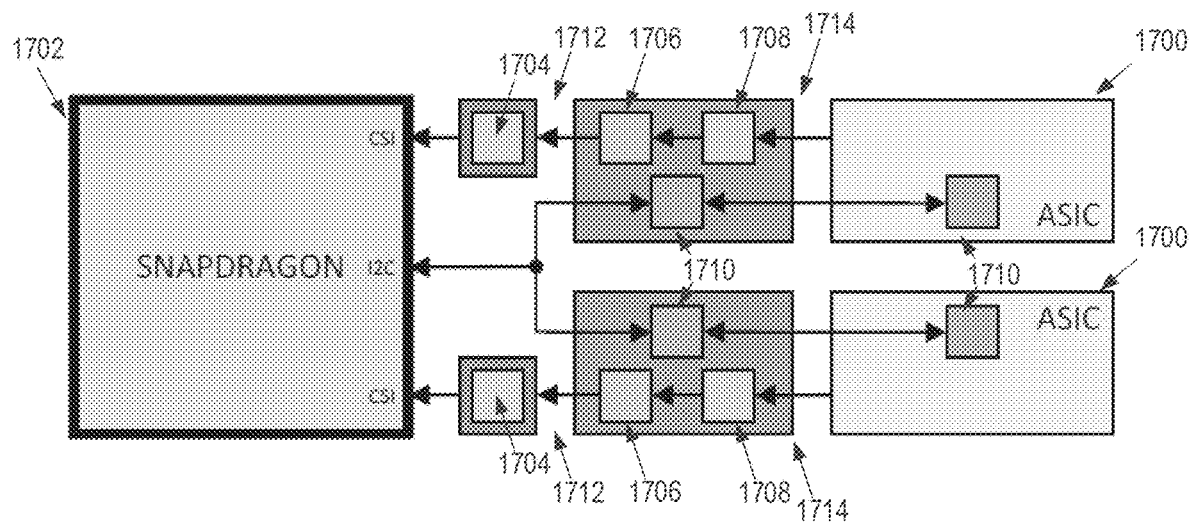
Figure 17D:
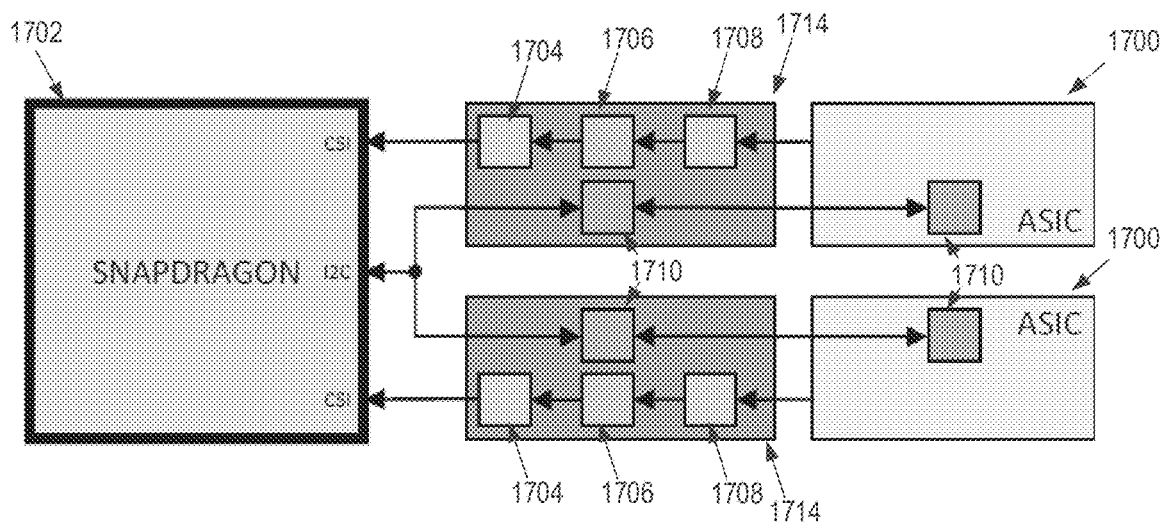

FIGS. 17A-D depict different example implementations for interfacing an ASIC as described throughout this document with an example controller for the PCU. The example components that are depicted across the various components in these figures are an ASIC 1700, a PCU controller 1702 (e.g., SNAPDRAGON processor), a digital I/O interface 1704, digital control layers 1706, transmit layers 1708, a command control interface 1710, a bridge chip 1712 (e.g., Meticom Bridge chip), and a field programmable gate array (FPGA) 1714. FIG. 17A depicts an integrated ASIC solution in which the digital interface, control, and transmit layers are included on the ASIC 1700. FIG. 17B depicts a hybrid ASIC solution in which the digital interface is moved from the ASIC 1700 onto a bridge chip 1712. FIG. 17C depicts a hybrid FPGA solution in which the digital interface is on the bridge chip 1712 and in which the digital control and transmit layers are integrated onto an FGPA 1714. FIG. 17D depicts in integrated FPGA solution in which the digital interface is also moved onto the FGPA 1714. Combinations and/or variations on these example solutions are also possible.

In one embodiment, a system for measuring an analyte in a sample includes a first graphene sensor, the first sensor configured to detect a first analyte. The system further includes an application specific integrated circuit (ASIC) electrically connected to the first graphene sensor and configured to receive electrical signals from the first graphene sensor and converting the electrical signals from the first graphene sensor into digital signals. In one alternative, the first graphene sensor detects the first analyte without the use of a reagent. In another alternative, the system is reagentless. In another alternative, the first graphene sensor includes one of a nucleic acid sequence and an antibody for detecting the first analyte. Alternatively, the ASIC includes a Wheatstone Bridge circuit interconnected with the first graphene sensor, the Wheatstone Bridge configured to detect resistance changes in the first graphene sensor. In another alternative, the Wheatstone Bridge is interconnected with an analog-to-digital converter, which converts an analog signal from the Wheatstone Bridge into the digital signals. Alternatively, the system further includes a second graphene sensor configured to detect a second analyte, wherein the ASIC is configured to convert electrical signals from the second graphene sensor into the digital signals, wherein the first and second graphene sensor function at the same time for a sample. Alternatively, the first and second analyte are different. In another alternative, the first analyte is a DNA/RNA sequence and the second analyte is a protein. Optionally, the system further includes a processing/sensing unit (PSU) that includes the first graphene sensor and the ASIC. Alternatively, the PSU is a cartridge. Optionally, the PSU includes a sample receiving area for receiving a sample. In one configuration, the PSU includes a preprocessing region configured to process the sample before it reaches the first graphene sensor. Optionally, the preprocessing region includes an electro-acoustic lysis module configured to lyse cells in the sample.

In one embodiment, a multiplexed analyte detection system includes a sample application area for receiving a sample. The system further includes a plurality of channels connected to the sample application area, wherein each of the plurality of channels include a graphene sensor of a plurality of graphene sensors configured to detect an analyte. The system further includes an application specific integrated circuit (ASIC) electrically connected to the plurality of graphene sensor in the plurality of channels and configured to receive electrical signals from the plurality of graphene sensors and converting the electrical signals from the plurality of graphene sensors into digital signals. In one alternative, each of the plurality of channels includes a preprocessing region for processing a portion of the sample. In another alternative, the system further includes a preprocessing region for processing the sample. Alternatively, the processing includes lysing the cells. Alternatively, each of the plurality of graphene sensors includes one of a plurality of biological probes. Optionally, each of the plurality of biological probes are selected a group consisting of a single strand of a nucleic acid, an antibody, and a protein. In another alternative, at least one of the plurality of biological probes is a single strand of nucleic acid and at least one of the plurality of biological probes is an antibody. Optionally, each of the plurality of graphene sensors spans one of the plurality of channels. In another alternative, one of a plurality of positive terminals is connected to one end of each of the plurality of graphene sensors and one of a plurality of negative terminals is connected to another end of each of the plurality of graphene sensors. Optionally, each of corresponding ones of the plurality of positive terminals and the plurality of negative terminals are connected to the ASIC. In another alternative, the system includes a preprocessing region configured to process the sample before the sample reaches the plurality of graphene sensors. Optionally, the preprocessing region includes an electro-acoustic lysis module configured to lyse cells in the sample. Alternatively, the electrical signals are representative of a change in resistance of the plurality of graphene sensors. Optionally, the first graphene sensor detects the first analyte without the use of a reagent. In another alternative, the system further includes a processing/sensing unit (PSU), the PSU including the sample application area, the plurality of channels, and the ASIC. Optionally, the system further includes a master control unit (MCU), the MCU in communication with the PSU and receiving the digital signals from the PSU and measuring one or more analytes in the sample.

In one embodiment, a multiplexed analyte detection system includes a sample application area for receiving a sample. The system further includes a plurality of channels connected to the sample application area, wherein each of the plurality of channels include a graphene sensor of a plurality of graphene sensors configured to detect an analyte. The system further includes an application specific integrated circuit (ASIC) electrically connected to the plurality of graphene sensor in the plurality of channels and configured to receive electrical signals from the plurality of graphene sensors and converting the electrical signals from the plurality of graphene sensors into digital signals. In one alternative, each of the plurality of channels includes a preprocessing region for processing a portion of the sample. In another alternative, the system further includes a preprocessing region for processing the sample. Alternatively, the processing includes lysing the cells. Optionally, each of the plurality of graphene sensors includes one of a plurality of biological probes. In another alternative, each of the plurality of biological probes are selected a group consisting of a single strand of a nucleic acid, an antibody, and a protein. Alternatively, at least one of the plurality of biological probes is a single strand of nucleic acid and at least one of the plurality of biological probes is an antibody. Optionally, each of the plurality of graphene sensors spans one of the plurality of channels. In another alternative, one of a plurality of positive terminals is connected to one end of each of the plurality of graphene sensors and one of a plurality of negative terminals is connected to another end of each of the plurality of graphene sensors and wherein each of corresponding ones of the plurality of positive terminals and the plurality of negative terminals are connected to the ASIC. Optionally, the system further includes a preprocessing region configured to process the sample before the sample reaches the plurality of graphene sensors. Optionally, the preprocessing region includes an electro-acoustic lysis module configured to lyse cells in the sample. Alternatively, the electrical signals are representative of a change in resistance of the plurality of graphene sensors. In another alternative, the first graphene sensor detects the first analyte without the use of a reagent. Optionally, the system further includes a processing/sensing unit (PSU), the PSU including the sample application area, the plurality of channels, and the ASIC. In another alternative, the system further includes a master control unit (MCU), the MCU in communication with the PSU and receiving the digital signals from the PSU and measuring one or more analytes in the sample. Optionally, the plurality of graphene sensors includes at least one graphene sensor for a first analyte of interest and at least one graphene sensor for a second analyte of interest and the first and second analyte of interest are different, and the at least one graphene sensor for the first analyte of interest and the at least one graphene sensor for the second analyte of interest are configured to analyze the sample. Optionally, the at least one graphene sensor for the first analyte of interest and the at least one graphene sensor for the second analyte of interest are configured to analyze the sample at the same time.

In one embodiment, a system for measuring an analyte in a sample includes a first graphene sensor, the first sensor configured to detect a first analyte. The system further includes an application specific integrated circuit (ASIC) electrically connected to the first graphene sensor and configured to receive electrical signals from the first graphene sensor and converting the electrical signals from the first graphene sensor into digital signals. Optionally, the system is reagentless. Alternatively, the first graphene sensor includes one of a nucleic acid sequence and an antibody for detecting the first analyte, the ASIC includes a Wheatstone Bridge circuit interconnected with the first graphene sensor, the Wheatstone Bridge configured to detect resistance changes in the first graphene sensor, and the Wheatstone Bridge is interconnected with an analog-to-digital converter, which converts an analog signal from the Wheatstone Bridge into the digital signals.

In one embodiment, a method of detecting an analyte includes providing a multiplexed analyte detection system. The multiplexed analyte detection system includes a sample application area for receiving a sample; a plurality of channels connected to the sample application area, wherein each of the plurality of channels include a graphene sensor of a plurality of graphene sensors configured to detect an analyte; and an application specific integrated circuit (ASIC) electrically connected to the plurality of graphene sensor in the plurality of channels and configured to receive electrical signals from the plurality of graphene sensors and converting the electrical signals from the plurality of graphene sensors into digital signals. The method further includes applying the sample to the sample application area and flowing the sample down the plurality of channels to the plurality of graphene sensors. The method further includes binding/hybridizing at least one analyte of interest to at least a portion of the plurality of graphene sensors. The method further includes detecting a change in resistance from the electrical signals at least a portion of the plurality of graphene sensors at the ASIC. The method further includes converting the change in resistance to the digital signals at the ASIC and calculating a result at a master control unit (MCU). Optionally, the result is a measurement of at least one analyte of interest. In one alternative, the result is a measurement of at least one analyte of interest. In another alternative, the method includes preprocessing the sample in a preprocessing area, wherein the preprocessing includes lysing cells that are included in the sample. Alternatively, the lysing is performed by an electro-acoustic lysis module.

In one embodiment, a system for detecting the presence, absence, or amount of one or more analytes in a sample, the system comprising at least one assay channel including a graphene sensor and an application specific integrated circuit (ASIC) electronically connected to the graphene sensor, the ASIC comprising a dedicated analog-to-digital signal processing unit configured to convert raw electronic signals generated by the graphene sensor into digital data that is specifically associated with the assay channel. In one alternative, the system comprises a plurality of assay channels. Alternatively, the plurality of assay channels includes from about 128 channels to 256 channels. In another alternative, the graphene sensor is functionalized with one or more biological probes. In another alternative, the ASIC is configured to control one or more processing steps to be performed within a processing region of the assay channel. Alternatively, the ASIC includes multiple independent and dedicated signal processing paths. Optionally, each signal processing path includes a positive and negative terminal that are electrically connected to the corresponding graphene sensor in the assay channel. In another alternative, each analog-to-digital signal processing unit comprises a signal amplifier, an analog-to-digital converter (ADC), a digital filter, a buffer, and an I/O interface. Alternatively, the assay channel comprises an input region configured to receive a portion of the sample inserted into the system, a processing region, and a detection region. Alternatively, the input region is configured to receive a portion of a sample inserted into the system. Optionally, the processing region is configured to prepare components within the sample for detection. Alternatively, the processing region is a cell lysis region configured to lyse cells within the sample. Optionally, the detection region is configured to include the graphene sensor, and wherein the graphene sensor includes a capture agent capable of binding to the one or more analytes. Alternatively, the assay channel includes a single-stranded nucleic acid attached to the graphene sensor. Optionally, the graphene-based sensor includes a capture agent that binds to NS1 polypeptides of a Zika virus. Alternatively, the one or more analytes comprises proteins, nucleic acids, intact cells, viruses, intact viruses, microorganisms, intact microorganisms, chemicals, and combination thereof.

In many embodiments, parts of the system are provided in devices including microprocessors. Various embodiments of the systems and methods described herein may be implemented fully or partially in software and/or firmware. This software and/or firmware may take the form of instructions contained in or on a non-transitory computer-readable storage medium. Those instructions then may be read and executed by one or more processors to enable performance of the operations described herein. The instructions may be in any suitable form such as, but not limited to, source code, compiled code, interpreted code, executable code, static code, dynamic code, and the like. Such a computer-readable medium may include any tangible non-transitory medium for storing information in a form readable by one or more computers such as, but not limited to, read only memory (ROM); random access memory (RAM); magnetic disk storage media; optical storage media; a flash memory, etc.

Embodiments of the systems and methods described herein may be implemented in a variety of systems including, but not limited to, smartphones, tablets, laptops, and combinations of computing devices and cloud computing resources. For instance, portions of the operations may occur in one device, and other operations may occur at a remote location, such as a remote server or servers. For instance, the collection of the data may occur at a smartphone, and the data analysis may occur at a server or in a cloud computing resource. Any single computing device or combination of computing devices may execute the methods described.

All publications, applications, references, and patents referred to in this application are herein incorporated by reference in their entirety. Other embodiments are within the claims.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A multiplexed analyte detection system, the system comprising:
a sample application area for receiving a sample;
a plurality of graphene sensors comprising channels connected to the sample application area; and
an application specific integrated circuit (ASIC) electrically connected to graphene sensors of the plurality of graphene sensor comprising channels and configured to receive electrical signals from the graphene sensors of the graphene sensor comprising channels.

2. The multiplexed analyte detection system of claim 1, wherein each of the plurality of graphene sensors comprising channels includes a preprocessing region for processing a portion of the sample.

3. The multiplexed analyte detection system of claim 1, further comprising a preprocessing region for processing the sample.

4. The multiplexed analyte detection system of claim 1, wherein each of the graphene sensors includes one of a plurality of biological probes.

5. The multiplexed analyte detection system of claim 4, wherein the biological probes are selected from the group consisting of a nucleic acid, an antibody and a protein.

6. The multiplexed analyte detection system of claim 4, wherein at least one of the biological probes is a single strand of nucleic acid and at least one of the biological probes is an antibody.

7. The multiplexed analyte detection system of claim 1, wherein each of the graphene sensors span the channel in which they are present.

8. The multiplexed analyte detection system of claim 1, further comprising a preprocessing region configured to process the sample before the sample reaches the graphene sensors.

9. The multiplexed analyte detection system of claim 8, wherein the preprocessing region includes an electro-acoustic lysis module configured to lyse cells in the sample.

10. The multiplexed analyte detection system of claim 1, wherein the electrical signals are representative of a change in resistance of the graphene sensors.

11. The multiplexed analyte detection system of claim 1, wherein a first graphene sensor of the graphene sensors is configured to detect a first analyte without the use of a reagent.

12. The multiplexed analyte detection system of claim 1, further comprising, a processing/sensing unit (PSU), the PSU including the sample application area, the plurality of channels, and the ASIC.

13. The multiplexed analyte detection system of claim 12, further comprising a master control unit (MCU), the MCU in communication with the PSU and receiving the digital signals from the PSU and measuring one or more analytes in the sample.

14. The multiplexed analyte detection system of claim 1, wherein the graphene sensors include at least a first graphene sensor for a first analyte of interest and at least a second graphene sensor for a second analyte of interest and the first and second analyte of interest are different.

15. The multiplexed analyte detection system of claim 14, wherein the at least one graphene sensor for the first analyte of interest and the at least one graphene sensor for the second analyte of interest are configured to analyze the sample at the same time.

16. The system of claim 14, wherein the system is reagentless.

17. The system of claim 14, wherein the first graphene sensor includes one of a nucleic acid sequence and an antibody for detecting the first analyte, the ASIC includes a Wheatstone Bridge circuit interconnected with the first graphene sensor, the Wheatstone Bridge is configured to detect resistance changes in the first graphene sensor, and the Wheatstone Bridge is interconnected with an analog-to-digital converter, which converts an analog signal from the Wheatstone Bridge into the digital signals.

18. A system for measuring an analyte in a sample, the system comprising:
a sample application area connected to a plurality of graphene sensors comprising channels; and
an application specific integrated circuit (ASIC) electrically connected to graphene sensors of the plurality of graphene sensors comprising channels.

19. A method of detecting whether an analyte is present in a sample, the method comprising:
applying the sample to a sample application area of a multiplexed analyte detection system that comprises:
a plurality of graphene sensors comprising channels connected to the sample application area; and
an application specific integrated circuit (ASIC) electrically connected to graphene sensors in the plurality of channels and configured to receive electrical signals from the graphene sensors; and
detecting a change in resistance from the received electrical signals to detect whether the analyte is present in the sample.

* * * * *

UNITED STATES PATENT AND TRADEMARK OFFICE
CERTIFICATE OF CORRECTION

PATENT NO. : 12,208,390 B2
APPLICATION NO. : 18/127933
DATED : January 28, 2025
INVENTOR(S) : John Lalonde et al.

It is certified that error appears in the above-identified patent and that said Letters Patent is hereby corrected as shown below:

In the Specification

Please replace "internet." with -- internet, -- (Column 3, Line 38).

Please replace "internet." with -- internet, -- (Column 3, Line 50).

Please replace "network." with -- network, -- (Column 3, Line 51).

Please replace "0.11" with -- 11 -- (Column 6, Line 18).

Please replace ""simultaneously."" with -- "simultaneously," -- (Column 6, Line 56).

Please replace "4." with -- 4, -- (Column 7, Line 50).

Please replace "virus." with -- virus, -- (Column 7, Line 54).

Please replace "HSV-2)." with -- HSV-2), -- (Column 7, Line 56).

Please replace "enterica)." with -- enterica), -- (Column 8, Line 21).

Please replace "gonorrhoeae." with -- gonorrhoeae, -- (Column 8, Lines 23-24).

Please replace "trachomatis." with -- trachomatis, -- (Column 8, Line 24).

Please replace "parvum." with -- parvum, -- (Column 8, Line 35).

Please replace "fragments." with -- fragments, -- (Column 8, Line 45).

Please replace "(p L)" with -- (μL) -- (Column 9, Line 12).

Signed and Sealed this
Fourteenth Day of October, 2025

John A. Squires
*Director of the United States Patent and Trademark Office*

CERTIFICATE OF CORRECTION (continued)
U.S. Pat. No. 12,208,390 B2

Please replace "limitation." with -- limitation, -- (Column 9, Line 67).

Please replace "limitation." with -- limitation, -- (Column 11, Line 16).

Please replace "virus." with -- virus, -- (Column 11, Line 21).

Please replace "virus." with -- virus, -- (Column 11, Line 22).

Please replace "DNA." with -- DNA, -- (Column 11, Line 31).

Please replace "RNA." with -- RNA, -- (Column 11, Line 60).

Please replace "(Ca$^+$)," with -- (Ca$^{++}$), -- (Column 12, Line 11).

Please replace "DNA." with -- DNA, -- (Column 12, Line 53).

Please replace "WAN." with -- WAN, -- (Column 14, Line 56).

Please replace "cases." with -- cases, -- (Column 15, Line 15).

Please replace "cases." with -- cases, -- (Column 15, Line 26).

Please replace "cases." with -- cases, -- (Column 15, Line 42).

Please replace "WAN." with -- WAN, -- (Column 15, Line 55).

Please replace "30)" with -- 300 -- (Column 18, Line 5).

Please replace "cases." with -- cases, -- (Column 18, Line 58).

Please replace "405." with -- 405, -- (Column 18, Line 65).

Please replace "cases." with -- cases, -- (Column 19, Line 22).

Please replace "WAN." with -- WAN, -- (Column 19, Line 29).

Please delete the space before "BLUETOOTH" (Column 19, Line 30).

Please replace "sample." with -- sample, -- (Column 20, Line 22).

Please replace "LAN." with -- LAN, -- (Column 20, Line 42).

Please replace "cases." with -- cases, -- (Column 20, Line 46).

Please replace "only." with -- only, -- (Column 20, Line 50).

CERTIFICATE OF CORRECTION (continued)
U.S. Pat. No. 12,208,390 B2

Please replace "interface." with -- interface, -- (Column 20, Line 65).

Please replace "520." with -- 520, -- (Column 22, Line 12).

Please replace "cases." with -- cases, -- (Column 22, Line 22).

Please replace "regions;" with -- regions: -- (Column 25, Line 24).

Please replace "-7C." with -- -7C, -- (Column 26, Line 61).

Please replace "(see." with -- (see, -- (Column 28, Line 66).

Please replace "Nanonaterials" with -- Nanomaterials -- (Column 29, Line 1).

Please replace "CH1p." with -- CH1p, -- (Column 31, Line 57).

In the Claims

Please replace "without the use" with -- without use -- in Claim 11 (Column 37, Line 43).

Please replace "receiving the digital" with -- receiving digital -- in Claim 13 (Column 38, Line 3).